(12) United States Patent
Ohara et al.

(10) Patent No.: US 9,125,409 B2
(45) Date of Patent: Sep. 8, 2015

(54) PLANT DISEASE CONTROL AGENT COMPRISING D-TAGATOSE AS ACTIVE INGREDIENT, AND PLANT DISEASE CONTROL METHOD

(75) Inventors: Toshiaki Ohara, Yasu (JP); Yutaka Ishida, Takamatsu (JP); Rika Kudou, Takamatsu (JP); Kazumasa Kakibuchi, Takamatsu (JP); Kazuya Akimitsu, Takamatsu (JP); Ken Izumori, Takamatsu (JP); Shigeyuki Tajima, Takamatsu (JP)

(73) Assignees: MITSUI CHEMICALS AGRO, INC., Tokyo (JP); NATIONAL UNIVERSITY CORPORATION KAGAWA UNIVERSITY, Kagawa (JP)

( * ) Notice: Subject to any disclaimer, the term of this patent is extended or adjusted under 35 U.S.C. 154(b) by 827 days.

(21) Appl. No.: 13/059,864

(22) PCT Filed: Aug. 18, 2009

(86) PCT No.: PCT/JP2009/003925
§ 371 (c)(1),
(2), (4) Date: Aug. 4, 2011

(87) PCT Pub. No.: WO2010/021121
PCT Pub. Date: Feb. 25, 2010

(65) Prior Publication Data
US 2011/0281807 A1    Nov. 17, 2011

(30) Foreign Application Priority Data
Aug. 18, 2008 (JP) ................ 2008-209921

(51) Int. Cl.
| | | |
|---|---|---|
| *A01N 63/04* | (2006.01) | |
| *A01N 65/00* | (2009.01) | |
| *A61K 31/70* | (2006.01) | |
| *A01N 43/16* | (2006.01) | |

(52) U.S. Cl.
CPC ..................... *A01N 43/16* (2013.01)

(58) Field of Classification Search
CPC .... A61K 31/7004; A01N 63/04; A01N 65/00
USPC ............. 536/1.11; 514/23, 384; 504/117, 140
See application file for complete search history.

(56) References Cited

U.S. PATENT DOCUMENTS

| | | | |
|---|---|---|---|
| 6,770,303 B1 | 8/2004 | Fritig et al. | |
| 2005/0245459 A1 | 11/2005 | Izumori et al. | |
| 2008/0182752 A1* | 7/2008 | Izumori et al. | 504/140 |
| 2009/0124679 A1* | 5/2009 | Mitani | 514/384 |

FOREIGN PATENT DOCUMENTS

| | | |
|---|---|---|
| JP | 2002-511495 A | 4/2002 |
| JP | 2004-300079 A | 10/2004 |
| JP | 2006-008669 A | 1/2006 |
| JP | 2006-188482 A | 7/2006 |
| WO | WO 03/097820 A1 | 11/2003 |

OTHER PUBLICATIONS

International Search Report (PCT/ISA/210) for PCT/JP2009/003925 dated Sep. 29, 2009.
Written Opinion (PCT/ISA/237) for PCT/JP2009/003925 dated Sep. 29, 2009.

* cited by examiner

*Primary Examiner* — Patrick Lewis
*Assistant Examiner* — Everett White
(74) *Attorney, Agent, or Firm* — Buchanan, Ingersoll & Rooney PC

(57) ABSTRACT

A plant disease control agent comprising at least one member selected from the group consisting of saccharides and substances each having a bactericidal and/or fungicidal activity. The plant disease control agents are effective for the control of cucumber, grape and cabbage downy mildew, damping-off in seedlings caused by *Pythium* spp, cucumber and barley powdery mildew, wheat stem rust, potato and tomato late blight, and others.

4 Claims, No Drawings

PLANT DISEASE CONTROL AGENT COMPRISING D-TAGATOSE AS ACTIVE INGREDIENT, AND PLANT DISEASE CONTROL METHOD

The present invention relates to a plant disease control agent comprising D-tagatose as an active ingredient, which is highly effective against various plant diseases, and to a method for preventing plant diseases by using the plant disease control agent comprising D-tagatose as an active ingredient.

In agricultural production, pest and disease control is one of the most important subjects, among which pesticides and herbicides become indispensable tools for pest and disease control and for labor-saving, respectively, for keeping the stable yields of crops and their quality, in the current agriculture to ensure food production. Many agrochemicals have been used. However, because of frequent and heavy use of structurally similar chemicals with the same mode of action, resistance problem of pests and plant pathogens against the chemicals has been become an urgent issue to be solved.

These days, the consumer's request for the reduction of pesticides to crops and the social demands for the reduction of the negative environmental impact caused by the chemical pesticides have been increasing. Under these circumstances, compositions comprising fungicides and methods for controlling plant diseases, which have less impact on environments, wider spectrum for various plant diseases and more effectiveness against plant diseases resistant to conventional fungicides are desired.

Most conventional pesticides directly target on pests and plant pathogens such as bacteria and fungi. In recent years, the chemicals such as probenazole, acibenzolar-S-methyl and so on, which activate an inherent biological defense mechanism of plant to induce its systemic acquired resistance to the plant diseases, have been developed. The induction of the systemic acquired resistance by activating an inherent biological defense mechanism of plant against various plant diseases is called as SAR, Systemic Acquired Resistance. Notably, probenazole has occupied a very large market of a rice blast fungicide. However, because of phytotoxicity registered crops in the pesticide labels of SAR chemicals are few. SAR chemicals, effective against various plant diseases on a wide variety of crops without any phytotoxicity, are desired worldwide.

Recently, many reports that the recognition of xenobiotics by plants is associated with the induction of the genes related to the plant defense pathways are known. The factors which induce the plant resistance genes are called as elicitors. (patent documents 1, 2 and non-patent document 1).

It is recognized that the elicitors are the substances which induce the defense pathways against plant diseases in plants and that as soon as the plants recognize the elicitors incorporated into the plants, the plants induce the plant defense mechanisms such as the production of fungicidal proteins and phytoalexins, the generation of activated oxygen and the cell death caused by its hypersensitive reaction and so on. Among saccharides, rare sugars such as D-psicose and D-allose have been reported to act as elicitors to induce the genes related to the plant defense pathways in plants and to be applicable to the plant protection agents. (Patent documents 3, 4)

In actual agricultural fields, many different kinds of diseases may occur at the same time and can be hardly controlled by one active ingredient of fungicide. The plant protection compositions are desired to show higher effectiveness at less dosage against to the plant diseases resistant to conventional fungicides. In order to prevent the development of the resistance to conventional fungicides, the plant protection composition comprising an active ingredient with a new chemical structure and a new mode of action, fungicides different from the conventional ones, and the new plant protection method using the aforedescribed composition are desired.

Under these circumstances, the combination of different types of fungicides has been studied for expecting the synergistically high plant protection at their reduced application dosage. However, the successful compositions comprising horticultural fungicides, such as inorganic cupper fungicides and azoxystrobin as active ingredients (Patent document 5) are the combinations of some specific chemical fungicides, but are not widely applicable to many other fungicides. And these compositions do not meet the consumer's need for the reduction of pesticide to crops and the social demands for the reduction of the negative environmental impact caused by the chemical pesticides.

D-tagatose, one of the rare sugars, which is used as a low calorie sweetener, a sweetness reinforcement and an additive material (Patent document 6,7) is considered to be safe to the environment including the human. As D-tagatose, as well as having a sweet taste, has a biochemical activity that inhibits the sugar catabolic enzyme in the small intestine, D-tagatose is expected to suppress the increase of blood glucose level and is attracting attention as a component of health food contributing to the diabetes prevention and so on. (Patent document 8, Non-patent document 2)

D-tagatose, as well as D-psicose and D-allose, induce a resistance gene in plants. (patent document 4) However, the induction of a group of resistance genes does not always result in the plant protection. Not only the plant protection activity of D-tagatose against various plant diseases, but the antimicrobial activity of D-tagatose has been uncertain.

PRIOR ARTS

Patent Documents

Patent Document 1: JP-A-2000-319107,
Patent Document 2: JP-A-1995-67681,
Patent Document 3: JP-A-2004-300079,
Patent Document 4: JP-A-2006-8669,
Patent Document 5: JP-A-2007-176865,
Patent Document 6: JP-A-2008-147,
Patent Document 7: JP-A-2002-500028,
Patent Document 8: JP-A-2008-189638
Non-patent Documents:
Non-patent Documents 1: Plant Cell Technology, Vol. 2, Supplement 1, p. 399, 1990
Non-patent Documents 2: Diabetes, Obesity and Metabolism, Vol.0, 2008, p. 109-134

DISCLOSURES OF THE INVENTION

Problems to be Solved by the Invention

The present invention improves the prior art and provides a plant disease control agent which shows a broad spectrum and a highly effective disease control without any phytotoxicity, and a method for controlling plant diseases using this agent.

Means for Solving the Problems

The present inventors newly found that D-tagatose shows high control efficacy against various plant diseases, such as powdery mildew, rust, and plant diseases caused by oomycota, and that as a result of conducting studies on the combination of D-tagatose with saccharides other than D-tagatose, or fungicidal and/or moldicidal materials. These combinations show unexpected higher synergistic control efficacy against those various plant diseases than each component does, which led to the completion of the present invention.

That is, the present invention is concerned with a plant disease control agent described in any of the following (a) to (h).

(a) A plant disease control agent, comprising D-tagatose as an active ingredient.
(b) A plant disease control agent, comprising a combination of D-tagatose with one or more saccharides other than D-tagatose, or fungicidal and/or moldcidal materials.
(c) A plant disease control agent according to claim 2, wherein saccharides are monosaccharides.
(d) A plant disease control agent according to (c), wherein monosaccharides are ones (c) selected at least one or more among D-fructose, D-psicose, D-sorbose or D-mannose.
(e) A plant disease control agent according to (b), wherein fungicidal and/or moldicidal materials are ones selected at least one or more among fungicides, moldicides or antibiotics.
(f) A plant disease control agent according to (b), wherein fungicidal and/or moldicidal materials are ones selected at least one or more compounds among the following fungicides such as (1) strobilurins, (2) triazoles, (3) imidazoles, (4) carboxamides, (5) acylalanines, (6) valinamides, (7) sulfonamides, (8) sulfenamides, (9) carbamates, (10) dithiocarbamates, (11) dicarboximides, (12) guanidines, (13) pyrimidines, (14) morpholines, (15) benzimidazoles, (16) pyrroles, (17) organophosphates, (18) coppers, (19) antibiotics, (20) organochloriness, (21) triazolopyrimidines, (22) benzoyls, (23) ethylenediamines, (24) isoxazolidines, (25) quinolines, and (26) thiazolidines
(g) A plant disease control agent according to (b), wherein fungicidal and/or moldicidal materials listed in (f) are compounds described from paragraph (0020) to paragraph (0025).
(h) A plant disease control agent according to (b), wherein fungicidal and/or moldicidal materials listed in (f) are compounds described in paragraph (0026).
(i) A plant disease control agent according to the above mentioned (a) to (h), of which diseases are caused by powdery mildew, rust fungi and oomycota And the present invention is concerned with a plant disease control method described in any of the following (j) and (k).
(j) A plant disease control method, characterized in applying plant disease control agent described in the above (a) to (i) to plants.
   (k) A plant disease control method described in the above (j), of which applying a plant disease control agent to plants means treating it to seeds, or mixing it in the soil of a cultivation beds.

ADVANTAGE OF THE INVENTION

D-Tagatose can be used as a foliar spray, a soil treatment or a seed treatment and other treatments. And these formulations, such as a foliar spray, a soil treatment and a seed treatment, show an excellent disease control efficacy against various plant diseases such as powdery mildew, rust and plant diseases caused by oomycota, including fungicide-resistant diseases, without any phytotoxicity to plants.

And the combination or the tank-mixing of D-tagatose with one or more substances selected from saccharides other than D-tagatose, or fungicidal and/or moldicidal materials, is able to show unexpected higher synergistic control efficacy against those various plant diseases than each component does. Furthermore, such synergistic efficacy may contribute not only to reduce the application dosage of these substances to plants, but to reduce the possible cause of their phytotoxicity. And the combination of the plant disease control agent described in the invention with the substances such as saccharides and/or fungicidal and moldicidal substances, of which the mode of actions are different from the agent, provide the plant disease control methods covering wider spectrum of various diseases.

D-Tagatose is one of so-called "rare sugars". The "rare sugar" can be defined as a monosaccharide that exists only in a small amount in nature and some of the rare sugars, such as D-psicose, D-tagatose, D-allose, D-talitol, D-allitol and so on have attracted attention as functional materials or natural bioactive substances. Some of the rare sugars, such as D-psicose and D-tagatose are able to be synthesized chemically (Carbohyd. Res., 70, 209 (1979)). And the production methods of rare sugars from monosaccharides that exist in a large amount in nature have been developed and rare sugars are able to be produced by using these methods (WO 03/097820). Furthermore, as an alternative to chemical synthesis, the method using biotechnology is ready to practical use. Biological methods using such biotechnology are advantageous because the substances with high purity can be obtained by enzymes specific to the substrates, and the biological methods are now applied to the production of various rare sugars.

In the present invention, D-tagatose can be used as a foliar spray, a soil treatment or a seed treatment and other treatments, and these formulations, such as a foliar spray, a soil treatment and a seed treatment, show an excellent disease control efficacy against various plant diseases, especially downy mildew on cucumber, cabbage and grapes, various damping-off diseases caused by *pythium*, powdery mildew on cucumber and barley, rust on wheat, and blight on potato and tomato, and other diseases. As described in this invention, D-tagatose is so highly effective against various plant diseases that D-tagatose is able to control plant diseases at the treatment timing of not only post-disease infestation but also pre-disease infection.

A plant disease control agent and a plant disease control method in the present invention, comprising D-tagatose as an active ingredient, may contain, if necessary, one or more sugars other than D-tagatose selected from the following sugars, such as monosaccharides, oligosaccharides, polysaccharides, neutral sugars, acidic sugars, aminosugars, sugar alcohols and their isomers. The sugars mentioned above include the following sugars, namely as monosaccharides D- and L-aldoses such as glucose, mannose, fructose, psicose, sorbose, allose, altrose, talose, galactose, idose, gulose, ribose, lyxose, xylose, arabinose, erythrose, threose and glyceraldehyde; D- and L-ketoses such as xylulose, ribulose, erythrulose and dihydroxyacetone; D- and L-sugar alcohols such as glucitol, mannitol, altritol, talitol, iditol, gulitol, allitol, galactitol, arabitol, xylitol, ribitol, erythritol, glycerine, maltitol, lactitol, inositol and quercitol; as disaccharides such as sucrose, maltose, lactose, cellobiose, trehalose and palatinose; as trisaccharides such as raffinose, panose, melezitose and gentianose; as tetrasaccharide stachyose. But the preset invention does not intend to limit above examples.

The combination of D-tagatose disclosed in this invention with saccharides other than D-tagatose shows higher synergistic control efficacy against various plant diseases than each component does.

The plant disease control agent of the present invention, comprising D-tagatose (a) as an active ingredient, can be used, if necessary, with the combination of fungicidal and/or moldcidal materials (b). In this invention, the materials (b) mean the one or more compounds selected from the chemical groups such as (1) strobilurin compounds, (2) triazole compounds, (3) imidazole compounds, (4) carboxamide compounds, (5) acylalanine compounds, (6) valinamide compounds, (7) sulfonamide compounds, (8) sulfenamide compounds, (9) carbamate compounds, (10) dithiocarbamate compounds, (11) dicarboximide compounds, (12) guanidine compounds, (13) pyrimidine compounds, (14) morpholine compounds, (15) benzimidazole compounds, (16) pyrrole compounds, (17) organophosphorus compounds, (18) copper compounds, (19) antibiotics, (20) organochlorine compounds, (21) triazolopyrimidine compounds, (22) benzoyl compounds, (23) ethylenediamine compound, (24) isoxazolidine compounds, (25) quinoline compounds, (26) thiazolidine compounds, (27) compound belonging to fungicides and moldicides.

Specific examples of compounds, antibiotics or fungicides and moldicides are listed below following above groups (1)-(27).

Group (1): Strobilurin Compounds of the Following 1-1~1-11

(1-1) azoxystrobin, (1-2) kresoxim-methyl, (1-3) pyraclostrobin, (1-4) picoxystrobin, (1-5)_fluoxastrobin, (1-6) dimoxystrobin, (1-7) orysastrobin, (1-8) metominostrobin, (1-9) trifloxystrobin, (1-10) pyrametostrobin, (1-11) pyraoxystrobin Group (2): Triazole Compounds of the Following 2-1~2-25

(2-1) simeconazole, (2-2) tebuconazole, (2-3) fenbuconazole, (2-4) hexaconazole, (2-5) imibenconazole, (2-6) triadimefon, (2-7) tetraconazole, (2-8) prothioconazole, (2-9) triticonazole, (2-10) epoxiconazole, (2-11) ipconazole, (2-12) metconazole, (2-13) propiconazole, (2-14) cyproconazole, (2-15) difenoconazole, (2-16) diniconazole, (2-17) fluquinconazole, (2-18) flusilazole, (2-19) penconazole, (2-20) bromuconazole, (2-21) triadimenol, (2-22) flutriafol, (2-23) myclobutanil, (2-24) etaconazole, (2-25) bitertanol Group (3): Imidazole Compounds of the Following 3-1~3-7

(3-1) oxpoconazole-fumarate, (3-2) triflumizole, (3-3) imazalil, (3-4) imazalil-S, (3-5) prochloraz, (3-6) pefurazoate, (3-7) triazoxide Group (4): Carboxamide Compounds of the Following 4-1~4-29

(4-1) penthiopyrad, (4-2) flutolanil, (4-3) furametpyr, (4-4) boscalid, (4-5) fenhexamid, (4-6) cyflufenamid, (4-7) tecloftalam, (4-8) picobenzamide, (4-9) mandipropamid, (4-10) bixafen, (4-11) carboxin, (4-12) oxycarboxin, (4-13) mepronil, (4-14)_silthiofam, (4-15) thifluzamide, (4-16) flumetover, (4-17) ethaboxam, (4-18) zoxamide, (4-19) tiadinil, (4-20) isotianil, (4-21) diclocymet, (4-22) fenoxanil, (4-23) fluopicolide, (4-24) fluopyram, (4-25) carpropamid, (4-26) tolfenpyrad, (4-27) penflufen, (4-28) sedaxane, (4-29) isopyrazam Group (5): Acylalanine Compounds of the Following 5-1~5-5

(5-1) metalaxyl, (5-2) metalaxyl-M, (5-3) benalaxyl, (5-4) benalaxyl-M, (5-5) furalaxyl-M Group (6): Valinamide Compounds of the Following 6-1~6-3

(6-1) benthiavalicarb-isopropyl, (6-2) iprovalicarb, (6-3) valifenalate

Group (7): Sulfonamide Compounds of the Following 7-1~7-3

(7-1) cyazofamid, (7-2) amisulbrom, (7-3) flusulfamide

Group (8): Sulfenamide Compounds of the Following 8-1~8-2

(8-1) tolylfluanid, (8-2) dichlofluanid

Group (9): Carbamate Compounds of the Following 9-1~9-4

(9-1) propamocarb, (9-2) propamocarb hydrochloride, (9-3) diethofencarb, (9-4) pyribencarb Group (10): Dithiocarbamate Compounds of the Following 10-1~10-8

(10-1) manzeb, (10-2) maneb, (10-3) propineb, (10-4) zineb, (10-5) metiram, (10-6) ziram, (10-7) thiuram, (10-8) polycarbamate Group (11): Dicarboximide Compounds of the Following 11-1~11-6

(11-1) iprodione, (11-2) procymidone, (11-3) captan, (11-4) vinclozolin, (11-5) chlozolinate, (11-6) folpet Group (12): Guanidine Compounds of the Following 12-1~12-4

(12-1) iminoctadine albesilate, (12-2) iminoctadine acetate, (12-3) guazatine, (12-4) dodine Group (13): Pyrimidine Compounds of the Following 13-1~13-9

(13-1) mepanipyrim, (13-2) fenarimol, (13-3) ferimzone, (13-4) cyprodinil, (13-5) pyrimethanil, (13-6) nuarimol, (13-7) dimethirimol, (13-8) bupirimate, (13-9) diflumetorim Group (14): Morpholine Compounds of the Following 14-1~14-5

(14-1) dimethomorph, (14-2) fenpropimorph, (14-3) tridemorph, (14-4) dodemorph, (14-5)_flumorph Group (15): Benzimidazole Compounds of the Following 15-1~15-6

(15-1) thiophanate-methyl, (15-2) thiophanate, (15-3) benomyl, (15-4) carbendazim, (15-5) thiabendazole, (15-6) fuberidazole Group (16): Pyrrole Compounds of the Following 16-1~16-3

(16-1) fludioxonil, (16-2) fluoroimide, (16-3) fenpiclonil

Group (17): Organophosphorous Compounds of the Following 17-1~17-5

(17-1) fosethyl and phosphite derivatives, (17-2) edifenphos, (17-3) tolclophos-methyl, (17-4) iprobenfos, (17-5) pyrazophos Group (18): Copper Compounds of the Following 18-1~18-10

(18-1) cupric hydroxide, (18-2) copper, (18-3) basic copper chloride, (18-4) basic copper sulfate, (18-5) oxine copper, (18-6) cupric sulphate pentahydrate, (18-7) cupric sulphate (anhydrous), (18-8) copper (nonylphenyl) sulphonate, (18-9) DBEDC, (18-10) dodecylbenzenesulphonic acid bisethylenediamine copper(II) complex Group (19): Antibiotics of the Following 19-1~19-8

(19-1) kasugamycin, (19-2) validamycin, (19-3) polyoxin derivatives, (19-4) blasticidin-S-benzylaminobenzenesulfonate, (19-5) streptomycin, (19-6) natamycin, (19-7) mildiomycin, (19-8) oxytetracycline Group (20): Organochlorine Compounds of the Following 20-1~20-3

(20-1) chlorothalonil, (20-2) fthalide, (20-3) quintozene

Group (21): Triazolopyrimidine Compounds of the Following 21-1~21-6

(21-1) 5-chloro-7-(4-methylpiperidine-1-yl)-6-(2,4,6-trifluorophenyl) [1,2,4]triazolo[1,5-a]pyrimidine, (21-2) 5-chloro-N-[(1S)-2,2,2-trifluoro-1-methylethyl]-6-(2,4,6-trifluorophenyl)[1,2,4]triazolo[1,5-a]pyrimidine, (21-3) 5-chloro-N-[(1R)-1,2-dimethylpropyl]-6-(2,4,6-trifluorophenyl)[1,2,4]triazolo[1,5-a]pyrimidine, (21-4) 5-(methoxymethyl)-6-octyl[1,2,4]triazolo[1,5-a]pyrimidine-7-amine, (21-5) 5-ethyl-6-octyl[1,2,4]triazolo[1,5-a]pyrimidine-7-amine, (21-6) ametoctradin Group (22): Benzoyl Compounds of the Following 22-1~22-2

(22-1) metrafenone, (22-2) 3-(2,3,4-trimethoxy-6-methylbenzoyl)-5-chloro-2-methoxy-4-methylpyridine Group (23): Ethylenediamine Compounds of the Following 23-1~23-9

(23-1) isopropyl((1S)-2-methyl-1-{[(4-methylbenzoyl)amino]methyl}propyl)carbamate, (23-2) isopropyl((1S)-2,2-methyl-1-{[(4-methylbenzoyl)amino]methyl}propyl)carbamate, (23-3) isopropyl((1S)-1-{[(1-benzofuran-2-ylcarbonyl)amino]methyl}-2-methylpropyl)carbamate, (23-4) 2,2,2-trifluoroethyl((1S)-2-methyl-1-{[(4-methylbenzoyl)amino]methyl}propyl)carbamate, (23-5) 2,2,2-trifluoroethyl((1S)-2,2-dimethyl-1-{[((4-methylbenzoyl)amino]methyl}propyl)carbamate, (23-6) 2,2,2-trifluoroethyl((1S)-1-{[(1-benzofurane-2-ylcarbonyl)amino]methyl}-2-methylpropyl)carbamate, (23-7) 2,2,2-trifluoroethyl{(1S)-1-methyl-2-[(4-methylbenzoyl)amino]ethyl}carbamate, (23-8) benzoyl((1S)-2-methyl-1-{[(4-methylbenzoyl)amino]methyl}propyl)carbamate, (23-9) isopropyl((1R)-2,2,2-trifluoro-1-{[(4-methylbenzoyl)amino]methyl}ethyl)carbamate Group (24): Isoxazolidine Compounds of the Following 24-1~24-2

(24-1) 3-[5-(4-chlorophenyl)-2,3-dimethylisoxazolidin-3-yl]pyridine, (24-2) 3-[2,3-dimethyl-5-(4-methylphenyl)isoxazolidin-3-yl]pyridine Group (25): Quinoline Compounds of the Following 25-1~25-3

(25-1) quinoxyfen, (25-2)[6-(2,2-dimethylethyl)-8-fluoro-2,3-dimethylquinoline-4-yl]acetate, (25-3) [6-(2,2-dimethylethyl)-8-fluoro-2,3-dimethylquinoline-4-yl]methoxyacetate Group (26): A Thiazolidine Compound 26-1

(26-1) flutianil

Group (27): Fungicidal and/or Moldicidal Compounds of the Following 27-1~27-49

(27-1) hymexazol, (27-2) fluazinam, (27-3) diclomezine, (27-4) tricyclazole, (27-5) cymoxanil, (27-6) famoxadone, (27-7) fenamidone, (27-8) chloropicrin, (27-9) thiadiazine, (27-10) proquinazid, (27-11) spiroxamine, (27-12) fenpropidine, (27-13) dithianon, (27-14) pencycuron, (27-15) isoprothiolane, (27-16) probenazole, (27-17) resveratrol, (27-18) triforine, (27-19) acibenzolar-S-methyl, (27-20) pyroquilon, (27-21) dinocap, (27-22) Nickel Organic, (27-23) etridiazole, (27-24) oxadixyl, (27-25) amobam, (27-26) pyrifenox, (27-27) oxolinic acid, (27-28) phosphoric acid, (27-29) dazomet, (27-30) methyl isothiocyanate, (27-31) methasulfocarb, (27-32) 1,3-dichloropropene, (27-33) carbam, (27-34) methyl Iodide, (27-35) sulfur, (27-36) Lime sulfur, (27-37) fentin hypochlorite, (27-38) chinomethionat, (27-39) chloroneb, (27-40) anilazine, (27-41) nitrothal-isopropyl, (27-42) fenitropan, (27-43) dicloran, (27-44)_benthiazole, (27-45) potassium bicarbonate, (27-46) sodium hydrogen carbonate, (27-47) sodium oleate, (27-48) fatty acid glycerides, (27-49) tebufloquin Judged from the experiments 1-23, among the compounds, antibiotics and/or fungicides or moldicies belonging to the above each group, the preferable ones are as follows;

Group (1): Strobilurin Compounds of the Following 1-1~1-11

(1-1) azoxystrobin, (1-2) kresoxim-methyl, (1-3) pyraclostrobin, (1-4) picoxystrobin, (1-5) fluoxastrobin, (1-6) dimoxystrobin, (1-7) orysastrobin, (1-8) metominostrobin, (1-9) trifloxystrobin, (1-10) pyrametostrobin, (1-11) pyraoxystrobin Group (2): Triazole Compounds of the Following 2-1~2-25

(2-1) simeconazole, (2-2) tebuconazole, (2-3) fenbuconazole, (2-4) hexaconazole, (2-5) imibenconazole, (2-6) triadimefon, (2-7) tetraconazole, (2-8) prothioconazole, (2-9) triticonazole, (2-10) epoxiconazole, (2-11) ipconazole, (2-12) metconazole, (2-13) propiconazole, (2-14) cyproconazole, (2-15) difenoconazole, (2-16) diniconazole, (2-17) fluquinconazole, (2-18) flusilazole, (2-19) penconazole, (2-20)_bromuconazole, (2-21) triadimenol, (2-22) flutriafol, (2-23) myclobutanil, (2-24) etaconazole, (2-25) bitertanol Group (3): Imidazole Compounds of the Following 3-1~3-7

(3-1) oxpoconazole-fumarate, (3-2) triflumizole, (3-3) imazalil, (3-4) imazalil-S, (3-5) prochloraz, (3-6) pefurazoate, (3-7) triazoxide Group (4): Carboxamide Compounds of the Following 4-1~4-29

(4-1) penthiopyrad, (4-2) flutolanil, (4-3) furametpyr, (4-4) boscalid, (4-5) fenhexamid, (4-6) cyflufenamid, (4-7) tecloftalam, (4-8) picobenzamide, (4-9) mandipropamid, (4-10) bixafen, (4-11) carboxin, (4-12) oxycarboxin, (4-13) mepronil, (4-14) silthiofam, (4-15) thifluzamide, (4-16)_flumetover, (4-17) ethaboxam, (4-18) zoxamide, (4-19) tiadinil, (4-20) isotianil, (4-21) diclocymet, (4-22) fenoxanil, (4-23) fluopicolide, (4-24) fluopyram, (4-25) carpropamid, (4-26) tolfenpyrad, (4-27) penflufen, (4-28) sedaxane, (4-29) isopyrazam Group (5): Acylalanine Compounds of the Following 5-1~5-5

(5-1) metalaxyl, (5-2) metalaxyl-M, (5-3) benalaxyl, (5-4) benalaxyl-M, (5-5)_furalaxyl-M Group (6): Valinamide Compounds of the Following 6-1~6-3

(6-1) benthiavalicarb-isopropyl, (6-2) iprovalicarb, (6-3) valifenalate

Group (7): Sulfonamide Compounds of the Following 7-1~7-3

(7-1) cyazofamid, (7-2) amisulbrom, (7-3) flusulfamide

Group (8): Sulfenamide Compounds of the Following 8-1~8-2

(8-1) tolylfluanid, (8-2) dichlofluanid

Group (9): Carbamate Compounds of the Following 9-1~9-4

(9-1) propamocarb, (9-2) propamocarb hydrochloride, (9-3) diethofencarb, (9-4) pyribencarb Group (10): Dithiocarbamate Compounds of the Following 10-1~10-8

(10-1) manzeb, (10-2) maneb, (10-3) propineb, (10-4) zineb, (10-5) metiram, (10-6) ziram, (10-7) thiuram, (10-8) polycarbamate Group (11): Dicarboximide Compounds of the Following 11-1~11-6

(11-1) iprodione, (11-2) procymidone, (11-3) captan, (11-4) vinclozolin, (11-5) chlozolinate, (11-6) folpet Group (12): Guanidine Compounds of the Following 12-1~12-4

(12-1) iminoctadine albesilate, (12-2) iminoctadine acetate, (12-3) guazatine, (12-4) dodine Group (13): Pyrimidine Compounds of the Following 13-1~13-5

(13-1) mepanipyrim, (13-2) fenarimol, (13-3) ferimzone, (13-4) cyprodinil, (13-5) pyrimethanil Group (14): Morpholine Compounds of the Following 14-1~14-5

(14-1) dimethomorph, (14-2) fenpropimorph, (14-3) tridemorph, (14-4) dodemorph, (14-5)_flumorph Group (15): Benzimidazole Compounds of the Following 15-1~15-6

(15-1) thiophanate-methyl, (15-2) thiophanate, (15-3) benomyl, (15-4) carbendazim, (15-5) thiabendazole, (15-6) fuberidazole Group (16): Pyrrole Compounds of the Following 16-1~16-3

(16-1) fludioxonil, (16-2) fluoroimide, (16-3) fenpiclonil

Group (17): Organophosphorous Compounds of the Following 17-1~17-3

(17-1) fosetyl and phosphite derivatives, (17-2) edifenphos, (17-3) tolclophos-methyl Group (18): Copper Compounds of the Following 18-1~18-7 and 18-10

(18-1) cupric hydroxide, (18-2) copper, (18-3) basic copper chloride, (18-4) basic copper sulfate, (18-5) oxine copper, (18-6) cupric sulphate pentahydrate, (18-7) cupric sulphate (anhydrous), (18-10) dodecylbenzenesulphonic acid bisethylenediamine copper(II) complex Group (19): Antibiotics of the Following 19-1~19-5

(19-1) kasugamycin, (19-2) validamycin, (19-3) polyoxin derivatives, (19-4) blasticidin-S-benzylaminobenzenesulfonate, (19-5) streptomycin Group (20): Organochlorine Compounds of the Following 20-1~20-3

(20-1) chlorothalonil, (20-2) fthalide, (20-3) quintozene

Group (21): Triazolopyrimidine Compounds of the Following 21-1~21-6

(21-1) 5-chloro-7-(4-methylpiperidine-1-yl)-6-(2,4,6-trifluorophenyl) [1,2,4]triazolo[1,5-a]pyrimidine, (21-2) 5-chloro-N-[(1S)-2,2,2-trifluoro-1-methylethyl]-6-(2,4,6-trifluorophenyl)[1,2,4]triazolo[1,5-a]pyrimidine, (21-3) 5-chloro-N-[(1R)-1,2-dimethylpropyl]-6-(2,4,6-trifluorophenyl)[1,2,4]triazolo[1,5-a]pyrimid ine, (21-4) 5-(methoxymethyl)-6-octyl[1,2,4]triazolo[1,5-a]pyrimidine-7-amine, (21-5) 5-ethyl-6-octyl[1,2,4]triazolo[1,5-a]pyrimidine-7-amine, (21-6) ametoctradin Group (22): Benzoyl Compounds of the Following 22-1~22-2

(22-1) metrafenone, (22-2) 3-(2,3,4-trimethoxy-6-methylbenzoyl)-5-chloro-2-methoxy-4-methylpyridine Group (23): Ethylenediamine Compounds of the Following 23-1~23-9

(23-1) isopropyl((1S)-2-methyl-1-{[(4-methylbenzoyl)amino]methyl}propyl)carbamate, (23-2) isopropyl((1S)-2,2-dimethyl-1-{[(4-methylbenzoyl)amino]methyl}propyl)carbamate, (23-3) isopropyl((1S)-1-{[(1-benzofuran-2-ylcarbonyl)amino]methyl}-2-methylpropyl)carbamate, (23-4) 2,2,2-trifluoroethyl((1S)-2-methyl-1-{[(4-methylbenzoyl)amino]methyl}propyl)carbamate, (23-5) 2,2,2-trifluoroethyl((1S)-2,2-dimethyl-1-{[((4-methylbenzoyl)amino]methyl}propyl)carbamate, (23-6) 2,2,2-trifluoroethyl((1S)-1-{[(1-benzofurane-2-ylcarbonyl)amino]methyl}-2-methylpropyl)carbamate, (23-7) 2,2,2-trifluoroethyl{(1S)-1-methyl-2-[(4-methylbenzoyl)amino]ethyl}carbamate, (23-8) benzoyl((1S)-2-methyl-1-{[(4-methylbenzoyl)amino]methyl}propyl)carbamate, (23-9) isopropyl((1R)-2,2,2-trifluoro-1-{[(4-methylbenzoyl)amino]methyl}ethyl)carbamate Group (24); Isoxazolidine Compounds of the Following 24-1~24-2

(24-1) 3-[5-(4-chlorophenyl)-2,3-dimethylisoxazoline-3-yl]pyridine, (24-2) 3-[2,3-dimethyl-5-(4-methylphenyl)isoxazoline-3-yl]pyridine Group (25); Quinoline Compounds of the Following 25-1~25-3

(25-1) quinoxyfen, (25-2)[6-(2,2-dimethylethyl)-8-fluoro-2,3-dimethylquinoline-4-yl]acetate, (25-3)[6-(2,2-Dimethylethyl)-8-fluoro-2,3-dimethylquinoline-4-yl]methoxyacetate Group (26); A Thiazolidine Compound 26-1

(26-1) flutianil

Group (27); Fungicidal and/or Moldicidal Compounds of the Following 27-1~27-21, 27-28 and 27-45~27-49

(27-1) hymexazol, (27-2) fluazinam, (27-3) diclomezine, (27-4) tricyclazole, (27-5) cymoxanil, (27-6) famoxadone, (27-7) fenamidone, (27-8) chloropicrin, (27-9) thiadiazine, (27-10) proquinazid, (27-11) spiroxamine, (27-12) fenpropidine, (27-13) dithianon, (27-14) pencycuron, (27-15) isoprothiolane, (27-16) probenazole, (27-17) resveratrol, (27-18) triforine, (27-19) acibenzolar-S-methyl, (27-20) pyroquilon, (27-21) dinocap, (27-28) phosphoric acid, (27-45) potassium bicarbonate, (27-46) sodium hydrogen carbonate, (27-47) sodium oleate, (27-48) fatty acid glycerides, (27-49) tebufloquin Among the compounds, antibiotics and/or fungicides or moldicides belonging to the groups mentioned above the more preferable ones are as follows;

Group (1); Strobilurin Compounds of the Following 1-1~1-5 and 1-7~1-9

(1-1) azoxystrobin, (1-2) kresoxim-methyl, (1-3) pyraclostrobin, (1-4) picoxystrobin, (1-5)_fluoxastrobin, (1-7) orysastrobin, (1-8) metominostrobin, (1-9) trifloxystrobin Group (2): Triazole Compounds of the Following 2-1~2-18

(2-1) simeconazole, (2-2) tebuconazole, (2-3) fenbuconazole, (2-4) hexaconazole, (2-5) imibenconazole, (2-6) triadimefon, (2-7) tetraconazole, (2-8)_prothioconazole, (2-14)_triticonazole, (2-10) epoxiconazole, (2-11) ipconazole, (2-12) metconazole, (2-13) propiconazole, (2-14) cyproconazole, (2-15) difenoconazole, (2-16) diniconazole, (2-17) fluquinconazole, (2-18) flusilazole Group (3): Imidazole Compounds of the Following 3-1~3-2

(3-1) oxpoconazole-fumarate, (3-2) triflumizole

Group (4): Carboxamide Compounds of the Following 4-1, 4-4~4-6, 4-9, 4-10, 4-17, 4-18, 4-23~4-25 and 4-27~4-29

(4-1) penthiopyrad, (4-4) boscalid, (4-5) fenhexamid, (4-6) cyflufenamid, (4-9) mandipropamid, (4-10) bixafen, (4-17) ethaboxam, (4-18) zoxamide, (4-23) fluopicolide, (4-24) fluopyram, (4-25) carpropamid, (4-27) penflufen, (4-28) sedaxane, (4-29) isopyrazam Group (5): Acylalanine Compounds of the Following 5-1~5-4

(5-1) metalaxyl, (5-2) metalaxyl-M, (5-3) benalaxyl, (5-4) benalaxyl-M

Group (6): Valinamide Compounds of the Following 6-1~6-3

(6-1) benthiavalicarb-isopropyl, (6-2) iprovalicarb, (6-3) valifenalate

Group (7): Sulfonamide Compounds of the Following 7-1~7-2

(7-1) cyazofamid, (7-2) amisulbrom

Group (9): Carbamate Compounds of the Following 9-1~9-2 and 9-4

(9-1) propamocarb, (9-2) propamocarb hydrochloride, (9-4) pyribencarb

Group (10): Dithiocarbamate Compounds of the Following 10-1~10-4, 10-6 and 10-7

(10-1) manzeb, (10-2) maneb, (10-3) propineb, (10-4) zineb, (10-6) ziram, (10-7) thiuram, Group (11): Dicarboximide Compounds of the Following 11-1~11-3

(11-1) iprodione, (11-2) procymidone, (11-3) captan

Group (12): Guanidine Compounds of the Following 12-1~12-2

(12-1) iminoctadine albesilate, (12-2) iminoctadine acetate

Group (13): Pyrimidine Compounds of the Following 13-1~13-5

(13-1) mepanipyrim, (13-2) fenarimol, (13-3) ferimzone, (13-4) cyprodinil, (13-5) pyrimethanil Group (14): Morpholine Compound of the Following 14-1

(14-1) dimethomorph

Group (15): Benzimidazole Compounds of the Following 15-1 and 15-3

(15-1) thiophanate-methyl, (15-3) benomyl

Group (16): Pyrrole Compound of the Following 16-1

(16-1) fludioxonil

Group (17): Organophosphorous Compounds of the Following 17-1
  (17-1) fosethyl and phosphite derivatives
Group (18): Copper Compounds of the Following 18-1
  (18-1) cupric hydroxide
Group (19): Antibiotics of the Following 19-1~19-4
  (19-1) kasugamycin, (19-2) validamycin, (19-3) polyoxin derivatives, (19-4) blasticidin-S-benzylaminobenzenesulfonate
Group (20): Organochlorine Compounds of the Following 20-1~20-2
  (20-1) chlorothalonil, (20-2) fthalide
Group (21): Triazolopyrimidine Compound of the Following 21-6
  (21-6) ametoctradin
Group (22): Benzoyl Compounds of the Following 22-1~22-2
  (22-1) metrafenone, (22-2) 3-(2,3,4-trimethoxy-6-methyl-benzoyl)-5-chloro-2-methoxy-4-methylpyridine
Group (25): Quinoline Compounds of the Following 25-1~25-2
  (25-1) quinoxyfen, (25-2)[6-(2,2-dimethylethyl)-8-fluoro-2,3-dimethylquinoline-4-yl]acetate,
Group (26): A Thiazolidine Compound 26-1
  (26-1) flutianil
Group (27): Fungicidal and/or Moldicidal Compounds of the Following 27-1, 27-2, 27-4~27-7 and 27-20
  (27-1) hymexazol, (27-2) fluazinam, (27-4) tricyclazole, (27-5) cymoxanil, (27-6) famoxadone, (27-7)_fenamidone, (27-20) pyroquilon A plant disease control agent of the present invention, comprising D-tagatose as an active ingredient, or comprising a combination of D-tagatose with one or more saccharides other than D-tagatose, or fungicidal and/or moldicidal materials, can be applied for plants separately or by mixed form. Usually the agent is applied with carriers or other constituents. If necessary, in a similar manner to the conventional agrichemical formulations, the plant disease control agent of the present invention can be formulated into with wettable powders, suspension concentrates, water dispersible granules, dusts, emulsifiable concentrates, granules and so on, added to the auxiliaries for formulation such as surfactants, wetting agents, sticking agents, thickener, preservatives, coloring agents, stabilizing agents and the like.

In helping the active ingredients to reach the site to be treated, synthetic or natural inorganic or organic materials that are usually formulated to facilitate storage, transportation and easy handling of the active ingredients, in either solid or liquid form, can be used as carriers. Carriers generally used for the agricultural and horticultural formulations are not limited for the invention.

For example, the solid carrier may be bentonite, montmorillonite, kaolinite, diatomite, activated clay, talc, clay, vermiculite, gypsum, calcium carbonate, amorphous-silica, inorganic substances such as ammonium sulfate, soybean powder, wood flour, sawdust, wheat flour, plant organic substances such as lactose, sucrose and glucose, and urea and the like. The liquid carrier may be aromatic hydrocarbons and naphthenes such as toluene, xylene, cumene and the like; paraffinic hydrocarbons such as n-paraffin, iso-paraffin, nujol, kerosene, mineral oil, polybutenes and the like; ketones such as acetone, methyl ethyl ketone and the like;, ethers such as dioxane, diethylene glycol, dimethyl ether and the like; alcohols such as ethanol, propanol, ethylene glycol and the like; carbonates such as ethylene carbonate, propylene carbonate, butylene carbonate and the like; aprotic solvents such as dimethylformamide, dimethyl sulfoxide and the like; and water.

In addition, to enhance the efficacy of a plant disease control agent of the present invention, comprising D-tagatose as an active ingredient, or comprising a combination of D-tagatose with one or more saccharides other than D-tagatose or fungicidal and/or moldcidal materials, the following adjuvant can be used individually or combination of the others depending on the type of the formulation and its application method. As the surfactant usually used in agrochemical formulations for the purpose of emulsifying, dispersion, spreading and wetting the following adjuvant can be mentioned but not be limited to these;

non-ionic surfactants such as sorbitan fatty acid esters, polyoxyethylene sorbitan fatty acid esters, sucrose fatty acid esters, polyoxyethylene fatty acid esters, polyoxyethylene resin acid esters, polyoxyethylene fatty acid diesters, polyoxyethylene castor oil, polyoxyethylene alkyl ethers; polyoxyethylene alkyl phenyl ethers, polyoxyethylene dialkyl phenyl ethers, formalin condensates of polyoxyethylene alkyl phenyl ethers, polyoxyethylene-polyoxypropylene block polymers, alkyl polyoxyethylene-polyoxypropylene Nock polymer ethers, alkyl phenyl polyoxyethylene-polyoxypropylene block polymer ethers, polyoxyethylene alkylamines, polyoxyethylene fatty acid amides, polyoxyethylene bisphenyl ethers, polyoxyalkylene benzyl phenyl ethers, polyoxyalkylene styryl phenyl ethers, and higher-alcohol polyoxyalkylene adduct- or polyoxyethylene ether- or ester-type silicon or fluorine-surfactants and the like;

anionic surfactants such as alkyl sulfates, polyoxyethylene alkyl ether sulfates, polyoxyethylene alkyl phenyl ether sulfates, polyoxyethylene benzyl phenyl ether sulfates, polyoxyethylene styryl phenyl ether sulfates, polyoxyethylene polyoxypropylene Nock polymer sulfates, paraffin sulfonates, alkane sulfonates, AOS, dialkyl sulfosuccinates, alkylbenzene sulfonates, naphthalene sulfonates, dialkyl naphthalene sulfonates, formalin condensates of naphthalene sulfonates, alkyl diphenyl ether disulfonates, lignin sulfonates, polyoxyethylene alkyl phenyl ether sulfonates, polyoxyethylene alkyl ether sulfosuccinic acid half esters, fatty acid salts, N-methyl-fatty acid sarcosinates, resin acid salts, polyoxyethylene alkyl ether phosphates, polyoxyethylene phenyl ether phosphates, polyoxyethylene dialkyl phenyl ether phosphates, polyoxyethylene benzylphenyl ether phosphates, polyoxyethylene benzylphenyl phenyl ether phosphates, polyoxyethylene styrylphenyl ether phosphates, polyoxyethylene styrylphenyl phenyl ether phosphates, polyoxyethylene polyoxypropylene Nock polymer phosphates, phosphatidylcholine, phosphatidyl ethanol imine and alkyl phosphates, alkyl phosphates and sodium tripolyphosphate and the like:

polyanionic polymer surfactants derived from acrylic acid, acrylonitrile, and acrylamidomethyl propanesulfonic acid;

cationic surfactants such as alkyltrimethylammonium chloride, methyl polyoxyethylene alkylammonium chloride, alkyl N-methylpyridinium bromide, monomethylammonium chloride, dialkylmethylammonium chloride, alkylpentamethylpropyleneamine dichloride, alkyldimethylbenzalkonium chloride, and benzethonium chloride, and ampholytic surfactants such as dialkyldiaminoethyl betain and alkyldimethylbenzyl betain. However, the surfactant is not limited to these examples.

As a binder, sodium alginate, polyvinyl alcohol, gum arabic, CMC sodium salt and bentonite, and the like are used. As a disintegrant, CMC sodium salt and croscarmellose sodium are used. As stabilizer, hindered phenol antioxidants and ultraviolet absorbers such as benzotriazoles and hindered amines, and the like are used. As pH controllers, phosphates, acetic acid and sodium hydroxide are used. Further, in order to prevent bacteria and fungi, industrial antibacterial and antifungal agent such as 1,2-benzoisothiazoline-3-one can be added. As the thickener, xanthan gum, guar gum, CMC sodium salt, gum arabic, polyvinyl alcohol and montmorillonite, and the like may be used. The defoaming agent such as a silicone compound, and the antifreezing agent such as propylene glycol and ethylene glycol, and the like, may be added as occasion demands. But the present invention is not limited to these examples described above.

Plant disease control methods of a composition comprising the plant diseases control agent of the present invention mean a foliar application on the plant, an incorporation into the nursery bed, a soil drench, a soil incorporation of the soil drenched with the plant diseases control agent of the present invention, an addition into a hydroponics and seed treatments such as spraying on the plant seeds, dust-coating on the plant seeds, dipping plant seeds and dust-coating, any of which exhibit a sufficient control effect against plant diseases when those skilled in the art use any of the above methods.

The application dosage and concentration of the composition comprising the plant diseases control agent of the present invention vary depending on target crops, target diseases, severeness of the diseases, formulation of the compound, application method, various kinds of environmental conditions and the like.

In case the composition of the present invention is treated as spraying or drenching, the amount of the active ingredients including D-tagatose and/or other components is suitably from 50 g/ha to 1,000,000 g/ha and preferably from 100 g/ha to 500,000 g/ha, and the amount of the active ingredients of other fungicides or moldicides except for D-tagatose in the composition of the present prevention is suitably from 1 g/ha to 10,000 g/ha and preferably from 10 g/ha to 5,000 g/ha. In case of D-tagatose seed treatment, the amount of D-tagatose is suitably from 0.001 g/1kg to 50 g/1kg of a seed and preferably from 0.01 g/1kg to 10 g/1kg of a seed, and the amount of the active ingredients of other fungicides or moldicides except for D-tagatose in the composition of the present prevention is preferably from 0.001 g/1kg to 50 g/1kg of a seed and preferably from 0.01 g/1kg to 10 g/1kg of a seed.

In case a plant disease control agent comprising D-tagatose as an active ingredient or a combination of D-tagatose and one or more saccharides other than D-tagatose, fungicidal and/or moldicidal materials is treated as foliar spraying on the foliar of plants, spraying on the soil surface, drenching, injecting into the soil or soil-drenching, the agent diluted with a suitable carrier to a certain concentration can be applied.

In case the plant disease control agent of the present invention is applied on seeds, the seeds can be dipped in the solution containing D-tagatose, or can be dipped in the agent diluted with a suitable carrier to a certain concentration, or can be dressed, sprayed or wiped by the agent diluted with a suitable carrier to a certain concentration.

In case dressing, spraying or wiping on seeds, the amount of the formulation of the agent is suitably from 0.05% to 50% of dry weight of seeds and preferably from 0.1% to 30% of dry weight of seeds, but the amount is not limited to these ranges mentioned above because it may vary by shape of seeds and by type of formulations. A suitable carrier can be a liquid such as water or an organic solvent like ethanol and the like, a solid carrier such as an inorganic material which is bentonite, montmorillonite, kaolinite, diatomite, activated clay, talc, clay, vermiculite, gypsum, calcium carbonate, amorphous-silica, inorganic substances such as ammonium sulfate and the like; vegetable organic materials such as soybean flour, wood flour, sawdust, wheat flour and the like and urea.

In the present invention, plants mean specifically rice, wheat, barley, corn, grape, apple, pear, peach, cherry, persimmon, citrus, soybean, green bean, strawberry, potato, cabbage lettuce, tomato, cucumber, eggplant, watermelon, beet, spinach, split pea, pumpkin, sugarcane, tobacco, green pepper, sweet potato, taro, konjac, cotton, sunflower, tulip, chrysanthemum and turf, etc, of which the whole parts, such as stems, leaves, roots, seeds and flowers are included.

In the present invention, plant seeds mean those storing nutrition for embryo plants to germinate and used for agricultural propagations, including specifically seeds of corn, soybean, cotton, rice, sugar beet, wheat, barley, sunflower, tomato, cucumber, eggplant, spinach, split pea, pumpkin, sugarcane, tobacco, green pepper, coleseed, etc.; seed tuber of aroid, potato, sweet potato, amorphophalus konjak, etc.; bulb of edible lily, tulip, etc.; or seed bulb of rakkyo, etc., and further include seeds and the like which have been subject to genetic transformation, such as seeds of soybean, corn, cotton, etc., which are imparted with herbicide resistant properties; or seeds of rice, tobacco, etc., which are adapted to cold regions; or seeds of corn, cotton, potato, etc., with insecticidal substance-producing properties. These plants are generated by artificial operation of genes and the like and do not originally exist in nature. Here, the present invention is not limited to these.

The plant disease control agent of the present invention can be used in combination with or together with other agrochemicals such as insecticides, miticides, nematocides, herbicides and plant growth regulators, soil conditioners and fertilizers.

The plant disease control methods of the present invention are effective against the following species of plant diseases.

Diseases and pathogens which are the targets of the present invention to control are specifically listed below, but the targets are not limited to these.

Concrete examples thereof include rice diseases such as blast (*Pyricularia oryzae*), sheath blight (*Rhizoctonia solani*), Helminthosporium leaf spot (*Cochliobolus miyabeanus*), "Bakanae"disease (*Gibberella fujikuroi*), seedling blight (*Pythium* spp., *Fusarium* spp., *Trichoderma* spp., *Rhizopus* spp., *Rhizoctonia solani* etc), false smut (*Claviceps virens*), kernel smut (*Tilletia barelayana*), downy mildew (*Sclerophthora macrospora*), bacterial leaf blight (*Xhanthomonas oryzae*), bacterial brown stripe (*Pseudomonas avenae*), bacterial palea browning (*Erwinia ananas*), bacterial seedling blight (*Burkholderia plantarii*), bacterial grain rot (*Burkholderia glumae*), sheath brown rot (*Pseudomonas fuscovaginae*);

wheat diseases such as powdery mildew (*Erysiphe graminis* f.sp. *hordei*; f.sp. *tritici*), rust (*Pucinia striiformis; P. graminis; P. recondita; P. hordei*), leaf spot (*Pyrenophora graminea*), net blotch (*Pyrenophora teres*), fusarium blight (*Fusarium graminearum, Fusarium culmorum, Fusarium avenaceum, Microdochium nivale*), snow blight and snow mold (*Typhula incarnata, Typhula ishikariensis, Micronectriella nivalis*), loose smut (*Ustilago nuda, Ustilago tritici, Ustilago nigra, Ustilago avenae*), bunt (*Tilletia caries, Tille-* tia pancicii), eye spot (*Pseudocercosporella herpotrichoides*), foot-rot (*Rhizoctonia cerealis*), leaf blotch (*Rhynchosporium secalis*), speckled leaf blotch (*Septoria tritici*), glume blotch (*Leptosphaeria nodorum*), seed rot (*Fusarium* spp., *Pythium* spp., *Rhizoctonia* spp., *Septoria nodorum, Pyrenophora* spp.), take-all (*Gaeumannomyces graminis*), anthracnose (*Colletotrichum gramaminicola*), ergot (*Claviceps purpurea*), spot blotch (*Cochliobolus sativus*), bacterial black node (*Pseudomonas syringae*);

corn diseases such as kernel rot (*Fusarium graminearum* etc), seedling blight (*Fusarium avenaceum, Penicillium* spp, *Pythium* spp., *Rhizoctonia* spp), rust (*Puccinia sorghi*), brown spot (*Cochliobolus heterostrophus*), smut (*Ustilago maydis*), anthracnose (*Colletotrichum gramaminicola*), northern leaf spot (*Cochliobolus carbonum*), grape diseases such as downy mildew (*Plasmopora viticola*), rust (*Phakopsora ampelopsidis*), powdery mildew (*Uncinula necator*), anthracnose (*Elsinoe ampelina*), ripe rot (*Glomerella cingulata*), black rot (*Guignardia bidwellii*), dead arm (*Phomopsis viticola*), fly speck (*Zygophiala jamaicensis*), gray mold (*Botrytis cinerea*), bud blight (*Diaporthe medusaea*), violet root rot (*Helicobasidium mompa*), white root rot (*Rosellinia necatrix*);

apple diseases such as powdery mildew (*Podosphaera leucotricha*), scab (*Venturia inaequalis*), alternaria leaf spot (*Alternaria alternata*(Apple pathotype)), rust (*Gymnosporangium yamadae*), blossom blight (*Monillia mali*), canker (*Valsa ceratosperma*), ring rot (*Botryosphaeria berengeriana*), bitter rot (*Colletotrichum acutatum*), fly speck (*Zygophiala jamaicensis*), sooty blotch (*Gloeodes pomigena*), fruit spot (*Mycosphaerella pomi*), violet root rot (*Helicobasidium mompa*), white root rot (*Rosellinia necatrix*), blight (*diaporthe canker*)(*Phomopsis mali, Diaporthe tanakae*), blotch (*Diplocarpon mali*), fire blight (*Erwinia amylovora*);

pear diseases such as black spot (*Alternaria kikuchiana*) (*Alternaria alternata*(Japanese pear pathotype)), scab (*Venturia nashicola*), rust (*Gymnosporangium haraeanum*), physalospora canker (*Physalospora piricola*), canker (*Diaporthe medusaea, Diaporthe eres*); pear disease such as phytophthora fruit rot (*Phytophthora cactorum*).

peach diseases such as scab (*Cladosporium carpophilum*), phomopsis rot (*Phomopsis* sp.), Phytophthora fruit rot (*Phytophthora* sp.), anthracnose (*Gloeosporium laeticolor*), bacterial shot hole (*Xhanthomonas campestris* pv. *pruni*); sweet cherry diseases such as anthracnose (*Glomerella cingulata*), young-fruit rot (*Monilinia kusanoi*), brown rot (*Monilinia fructicola*);

persimmon diseases such as anthracnose (*Gloeosporium kaki*), angular and circular leaf spot (*Cercoapora kaki; Mycosphaferella nawae*) (*Cercospora kaki; Mycosphaerella nawae*), powdery mildew (*Phyllactinia kakikora*);

citrus diseases such as melanose (*Diaporthe citri*), common green mold (*Penicillium digitatum*), blue mold (*Penicillium italicum*), scab (*Elsinoe fawcettii*), brown rot (*Phytophthora citrophthora*), canker (*Xhanthomonas campestris* pv. *citri*);

diseases of tomatoe, cucumber, bean, strawberry, potato, cabbage, eggplant, lettuce, etc., such as gray mold (*Botrytis cinerea*);

diseases of tomato, cucumber, bean, strawberry, potato, rapeseed, cabbage, eggplant, lettuce, etc such as sclerotinia rot (*Sclerotinia sclerotiorum*);

diseases of tomato, cucumber, beans, radish, watermelon, eggplant, rapeseed, pepper, spinach, sugar beet etc, such as damping-off (*Rhizoctonia* spp., *Pythium* spp., *Fusarium* spp., *Phythophthora* spp., *Sclerotinia sclerotiorum*, etc);

solanaceous plant disease such bacterial wilt (*Ralstonia solanacearum*); cucurbitaceae family diseases such as downy mildew (*Pseudoperonospora cubensis*), powdery mildew (*Sphaerotheca fuliginea*), anthracnose (*Colletotrichum lagenarium*), gummy stem blight (*Mycosphaerella melonis*), fusarium wilt (*Fusarium oxysporum*), phytophthora rot (*Phytophthora parasitica, Phytophthora melonis, Phytophthora nicotianae, Phytophthora drechsleri, Phytophthora capsici,* etc);

tomato diseases such as early blight (*Alternaria solani*), leaf mold (*Cladosporium fulvam*), late blight (*Phytophthora infestans*), fusarium wilt (*Fusarium oxysporum*), damping-off (*Pythium myriotylum, Pythium dissotocum*), anthracnose (*Colletotrichum phomoides*), bacterial canker (*Clavibacter michiganensis*); eggplant diseases such as powdery mildew (*Erysiphe cichoraceorum*) (*Sphaerotheca fuliginea* ect), leaf mold (*Mycovellosiella nattrassii*), late blight (*Phytophthora infestans*), Brown rot (*Phytophthora capsici*);

rape diseases such as gray leaf spot (*Alternaria brassicae*), cruciferous vegetable diseases such as alternaria leaf spot (*Alternaria brassicae* etc), leaf spot (*Cercosporella brassicae*), black leg (*Leptospheria maculans*), clubroot (*Plasmodiophora brassicae*), downy mildew (*Peronospora brassicae*);

cabbage disease such as head rot (*Rhizoctonia solani*), yellows (*Fusarium oxysporum*); chinese cabbage diseases such as bottom rot (*Rhizoctonia solani*), yellows (*Verticillium dahlie*); green onion diseases such as rust (*Puccinia allii*), alternaria leaf spot (*Alternaria porri*), southern blight (*Sclerotium rolfsii. Sclerotium rolfsii*), phytophthora rot (*Phytophthora porri*);

soybean diseases such as purple speck (*Cercospora kikuchii*), sphaceloma scab (*Elsinoe glycinnes*), pod and stem blight (*Diaporthe phaseololum*), rhizoctonia root rot (*Rhizoctonia solani*), phytophthora rot (*Phytophthora megasperma*), downy mildew (*Peronospora manshurica*), rust (*Phakopsora pachyrhizi*), anthracnose (*Colletotrichum truncatum*);

kidney bean diseases such as anthracnose (*Colletotrichum lindemuthianum*); peanut diseases such as leaf spot (*Mycosphaerella personatum*) and brown leaf spot (*Cercospora arachidicola*); pea diseases such as powdery mildew (*Erysiphe pisi*), downy mildew (*Peronospora pisi*), bacterial blight (*Pseudomonas syringae* pr. *pisi*); broad bean diseases such as downy mildew (*Peronospora viciae*), phytophthora rot (*Phytophthora nicotianae*); potato diseases such as early blight (*Alternaria solani*), black scurf (*Rhizoctonia solani*), late blight (*Phytophthora infestans*), silver scurf (*Spondylocladium atrovirens*), dry rot (*Fusarium oxysporum, Fusarium solani*), powdery scab (*Spongospora subterranea*); beet diseases such as cercospora leaf spot (*Cercospora beticola*), downy mildew (*Peronospora schachtii*), black root rot (*Aphanomyces cochioides*), Phoma root rot (*Phoma batae*), scab (*Streptomyces scabies*);

carrot diseases such as leaf bright (*Alternaria dauci*); strawberry diseases such as powdery mildew (*Sphaerotheca humuli*), phytophthora rot (*Phytophthora nicotianae*), crown rot (*Colletotrichum acutatum, Gromerella cingulata*), soft rot (*Pythium ultimum Trow* var. *ultimum*)

tea diseases such as net blister blight (*Exobasidium reticulatum*), white scab (*Elsinoe leucospila*), anthracnose (*Colletotrichum theae sinensis*), gray blight (*Pestalotiopsis longiseta*) tobacco diseases such as brown spot (*Alternaria alternata*(Tobacco pathotype)), powdery mildew (*Erysiphe cichoracearum*), anthracnose (*Colletotrichum tabacum*), black shank (*Phytophthora parasitica*), wild fire (*Pseudomonas syringae* pr. *tabaci*);

cotton diseases such as fusarium wilt (*Fusarium oxysporum*); sunflower diseases such as sclerotinia rot (*Sclerotinia sclerotiorum*); rose diseases such as black spot (*Diplocarpon rosae*), powdery mildew (*Sphaerotheca pannosa*), phytophthora disease (*Phytophthora megasperma*), downy mildew (*Peronospora sparsa*); chrysanthemum diseases such as leaf blotch (*Septoria chrysanthemi-indici*), rust (*Puccinia horiana*) and phytophthora blight (*Phytophthora cactorum*)

turf disease such as brown patch (*Rhizoctonia solani*), dollar spot (*Sclerotinia homoeocarpa*), curvularia leaf blight (*Curvularia geniculata*), rust (*Puccinia zoysiae*), helminthosporium leaf blight (*Cochliobolus* ap.), scald (*Rhynchosporium secalis*), take-all (*Gaeumannomyces graminis*), anthracnose (*Colletotrichum graminicola*), typhula snow blight (*Typhula incarnata*), typhula snow blight (*Typhula ishikariensis*), sclerotinia snow blight (*Sclerotinia borealis*), fairy ring (*Marasmius oreades* etc), pythium red blight (*Pythium aphanidermatum* etc), blast (*Pyricularia oryzae*)

Although the present invention is more specifically described in further detail below with reference to examples, the present invention is not limited to these examples.

EXAMPLE 1

This example shows the disease control test on cucumber downy mildew (pot test: preventive effect).

Test plants (cucumber, variety: Sagami hanpaku) were seeded and grown until the one true leaf stage. D-Tagatose was diluted to 5%, 1% and 0.5% with distilled water and then 10 ml of the dilution was sprayed on the test plant. Three or five days after spraying, a sporangium suspension of *Pseudoperonospora cubensis* containing $1\times10^3$/ml were inoculated by spraying on test plants and then the plants were put for 16 hours in an incubation chamber (20° C. to 23° C.) to promote disease. Seven days after inoculation the disease severity of the test plants was observed and the effectiveness of test sample was judged. Tests were carried out using two plants for each test set and the disease severity of the test plants was judged in accordance with the following criteria. The preventive value was calculated from the degree of the disease severity.

[Disease Severity]
0 (No lesion)
1 (Lesion area was not more than 40%)
2 ((Lesion area was 40%-80%)
3 (Lesion area was not less than 80%)
[Preventive Value]
Preventive value=100{1−(n/N)}
N=disease severity of untreated leaf, n=disease severity of the tested leaf

TABLE 1

| Compounds | Treated Concentration(ppm) | Preventive value (3 DAS*) | Preventive value (5 DAS*) |
|---|---|---|---|
| 1 D-Tagatose | 50000 | 100.0 | 100.0 |
|  | 10000 | 99.2 | 90.0 |
|  | 5000 | 49.2 | 37.5 |
| 2 D-Glucose | 50000 | 0.0 | 0.0 |
|  | 10000 | 0.0 | 0.0 |
|  | 5000 | 0.0 | 0.0 |
| 3 Probenazole | 100 | 33.3 | 95.0 |
| 4 Acibenzolar-S-Methyl | 50 | 91.7 | 99.2 |
| 5 Metalaxyl | 300 | 100.0 | 100.0 |
| 6 Untreated |  | — | — |

*DAS: days after spraying

As the result of this test, the preventive values of the D-tagatose solution of 5%, 1% and 0.5% were 100, 99.2 and 49.2, 3 days after the inoculation and were 100, 90, 37.5, 5 days after inoculation, respectively. The higher concentration of D-tagatose resulted in the higher preventive effect.

EXAMPLE 2

This example shows the disease control test on cucumber downy mildew (pot test: curative effect).

Test plants (cucumber, variety: Sagami hanpaku) were seeded and grown until the one true leaf stage. And then a sporangium suspension of *Pseudoperonospora cubensis* containing $1\times10^3$/ml were sprayed on the back side of the leaves of test plants for inoculation and then the plants were put for 16 hours in an inoculation chamber (20° C. to 23° C.) to promote disease. For a curative test, the inoculated plants as described above were used.

D-Tagatose was diluted to 5%, 1% and 0.5% with distilled water and then 10ml of the dilution was sprayed on the test plant. Seven days after the spraying of D-tagatose the disease severity of the test plants was observed and the effectiveness of test sample was judged. Tests were carried out using two plants for each test set and the disease severity of the test plants was judged. The control value was calculated from the degree of disease severity as in Example 1.

TABLE 2

| Compounds | Treated concentration(ppm) | Preventive value |
|---|---|---|
| 1 D-Tagatose | 50000 | 100.0 |
|  | 10000 | 91.7 |
|  | 5000 | 22.5 |
| 2 D-Glucose | 50000 | 0.0 |
|  | 10000 | 0.0 |
|  | 5000 | 0.0 |
| 3 Probenazole | 100 | 18.3 |
| 4 Acibenzolar-S-Methyl | 50 | 25.0 |
| 5 Metalaxyl | 300 | 100.0 |
| 6 Untreated |  | — |

The result of this test shows, the control values of the D-tagatose solution of 5%, 1% and 0.5% were 100, 91.7 and 22.5, respectively. The higher concentration of D-tagatose resulted in the higher preventive effect. And D-tagatose was effective enough at this test condition, at which plant activators are not effective.

EXAMPLE 3

This example shows the disease control test on cucumber downy mildew (pot test: soil drench test).

Test plants (cucumber, variety: Sagami hanpaku) were seeded and grown until the one true leaf stage. D-Tagatose was diluted to 5% and 1% with distilled water and then 5ml of the dilution was drenched into the soil of the pot. Five days after drenching, a sporangium suspension of *Pseudoperonospora cubensis* containing $1\times10^3$/ml were inoculated by spraying on the test plants and then put them for 16 hours in an inoculation chamber (20° C. to 23° C.) to promote disease. Seven days after inoculation the disease severity of the test plants was observed and the effectiveness of test sample was judged. Tests were carried out using two plants for each test set and the disease severity of the test plants was judged. The preventive value was calculated from the degree of disease severity as in Example 1.

TABLE 3

| | Compounds | Treated concentration(ppm) | Preventive value |
|---|---|---|---|
| 1 | D-Tagatose | 50000 | 100.0 |
| | | 10000 | 95.0 |
| 2 | D-Glucose | 50000 | 0.0 |
| | | 10000 | 0.0 |
| 5 | Metalaxyl | 300 | 100.0 |
| 6 | Untreated | — | |

The result of this test shows the preventive values of the D-tagatose solution 5% and 1% were 100, and 95, respectively. D-Tagatose at drench treatment was effective enough.

EXAMPLE 4

This example shows the disease control test on cucumber downy mildew (field trial).

Test plants (cucumber, variety: Sagami hanpaku) were planted and grown until the 10 leaves stage. D-Tagatose was diluted to 5% and 1% solution with distilled water and sprayed on the plants three times every 7 days. After the first spraying of the dilution, a sporangium suspension of *Pseudoperonospora cubensis* containing $1 \times 10^5$/ml were inoculated by spraying on the test plants. The disease severity of the test plants was observed and the effectiveness of test sample was judged. Tests were carried out in duplicate using 8 plants for each test set and the disease severity of the test plants was judged in accordance with the following criteria. The preventive value was calculated from the degree of disease severity.

[Disease Severity]
0 (No lesion)
1 (Lesion area was not more than 5% of the leaves)
2 ((Lesion area was 5%-25% of the leaves)
3 (Lesion area was 25%-50% of the leaves)
4 (Lesion area was not less than 50% of the leaves)
[Disease Severity of Each Field Test and Preventive Value]
Degree of disease severity=$100 \times \{(1n+2n+3n+4n)/4N)\}$
N=number of leaves observed
n=number of leaves among N, which shows each disease severity
Preventive value=$100\{1-(n/N)\}$
N=Degree of disease severity of untreated plant, n=Degree of disease severity of the treated plant The result of this test shows the preventive values of the D-tagatose solution 5% and 1% were 96.1 and 96.5, respectively. D-Tagatose at the field test was effective enough.

EXAMPLE 5

This example shows the disease control test on cucumber damping-off (pot test: soil drench test).

Five seeds of test plants (cucumber, variety: Sagami hanpaku) were sowed in a pot (5×5 cm), which contains infested soil with *Pythium aphanidermatum* (mycelium 100g/1L soil) and the seeds were covered with the soil. The pot was drenched with 10 ml of D-tagatose dilution. After 2 weeks, the disease severity of the test plants was observed and the effectiveness of test sample was judged. Tests were carried out in triplicate using 5 plants for each test set and the preventive value was calculated from the germination rate.

TABLE 5

| | Compounds | Treated concentration (ppm) | Preventive value |
|---|---|---|---|
| 1 | D-Tagatose | 50000 | 92.5 |
| | | 10000 | 70.0 |
| 2 | D-Glucose | 50000 | 0.0 |
| | | 10000 | 0.0 |
| 5 | Metalaxyl | 300 | 95.0 |
| 6 | Untreated | — | |

The result of this test shows the preventive values of the tests drenched with D-tagatose solution 5% and 1% were 92.5 and 70.0, respectively. D-Tagatose was effective enough against cucumber damping-off.

EXAMPLE 6

This example shows the disease control test on tomato late blight (pot test: preventive effect).

Test plants (tomato, variety: Ogata-fukujyu) were seeded and grown until the three leaf stage.

D-Tagatose was diluted to 10% and 5% with distilled water and then 10ml of the dilution was sprayed on the test plants. Three days after spraying the solution, a sporangium suspen-

TABLE 4

| | Compounds | Treated con. (ppm) | | N | Disease severity | | | | | n/N × 100 | D.D.S | P.V. |
|---|---|---|---|---|---|---|---|---|---|---|---|---|
| | | | | | 0 | 1 | 2 | 3 | 4 | | | |
| 1 | D-Tagatose | 50000 | a | 50 | 44 | 6 | 0 | 0 | 0 | 12.0 | 3.00 | 95.4 |
| | | | b | 50 | 46 | 4 | 0 | 0 | 0 | 8.0 | 2.00 | 96.9 |
| | | | Av | | | | | | | 10.0 | 2.50 | 96.1 |
| 2 | D-Tagatose | 10000 | a | 50 | 44 | 6 | 0 | 0 | 0 | 12.0 | 3.00 | 95.4 |
| | | | b | 50 | 47 | 3 | 0 | 0 | 0 | 6.0 | 1.50 | 97.7 |
| | | | Av | | | | | | | 9.0 | 2.25 | 96.5 |
| 3 | Metalaxyl + Manzeb(WP) (ai: 10% + 55%) | 100 + 550 | a | 50 | 33 | 12 | 1 | 2 | 2 | 34.0 | 14.00 | 78.4 |
| | | | b | 50 | 20 | 16 | 1 | 1 | 2 | 40.0 | 14.50 | 77.6 |
| | | | Av | | | | | | | 37.0 | 14.25 | 78.0 |
| 4 | Cyazofamid (FL) (ai. 9.4%) | 94 | a | 50 | 37 | 8 | 4 | 1 | 0 | 26.0 | 9.50 | 85.3 |
| | | | b | 50 | 47 | 3 | 0 | 0 | 0 | 6.0 | 1.50 | 97.7 |
| | | | Av | | | | | | | 16.0 | 5.50 | 91.5 |
| 5 | Untreated | | a | 50 | 1 | 4 | 13 | 12 | 20 | 98.0 | 73.00 | — |
| | | | b | 50 | 1 | 15 | 14 | 10 | 10 | 98.0 | 56.50 | — |
| | | | Av | | | | | | | 98.0 | 64.75 | — |

D.D.S.: Degree of disease severity,
P.V.: Preventive value sion of *Phytophthora infestans* containing 1×10³/ml were inoculated by spraying on test plants and then put them for 16 hours in an inoculation chamber (20° C. to 23° C.) to promote disease. Seven days after infection inoculation the disease severity of the test plants was observed and the effectiveness of test sample was judged. Tests were carried out using two plants for each test set and the disease severity of the test plants was judged in accordance with the following criteria. The preventive value was calculated from the degree of disease severity as in Example 1.

TABLE 6

| | Compounds | Treated concentration (ppm) | Preventive value |
|---|---|---|---|
| 1 | D-Tagatose | 100000 | 58.3 |
| | | 50000 | 28.3 |
| 2 | D-Glucose | 100000 | 0.0 |
| | | 50000 | 0.0 |
| 5 | Metalaxyl | 300 | 93.3 |
| 6 | Untreated | — | — |

The result of this test shows the preventive values of the tests sprayed with D-tagatose solution 10% and 5% were 58.3 and 28.3, respectively. D-Tagatose was effective enough against tomato phytophthora rot.

EXAMPLE 7

This example shows the disease control test on cucumber downy mildew (pot test: preventive effect of a combination of D-tagatose with saccharides other than D-tagatose).

Test plants (cucumber, variety: Sagami hanpaku) were seeded and grown until the one true leaf stage. D-tagatose alone was diluted to 5%, 1%, 0.5% and 0.1%, and the combination of D-tagatose and other saccharide were diluted to be 0.5% and 0.5% solution respectively with distilled water, and then 10ml of the dilution was sprayed on the test plant. Three days after spraying of the solution, a sporangium suspension of *Pseudoperonospora cubensis* containing 1×10³/ml were inoculated by spraying on test plants and then put them for 16 hours in an inoculation chamber (20° C. to 23° C.) to promote disease. Seven days after inoculation the disease severity of the test plants was observed and the effectiveness of test sample was judged. Tests were carried out using two plants for each test set and the disease severity of the test plants was judged in accordance with the following criteria. The preventive value was calculated from the degree of disease severity as in example 1.

Synergistic effect was determined by the Colby's equation below.

$$E=(X+Y)-(X*Y)/100$$

X is the observed effect, in percentage, of the first active ingredient, and

Y is the observed effect, in percentage, of the second active ingredient.

E is the effect, in percentage, of the mixture expected from additive contribution of the individual components.

E, X and Y: 100 means prefect control effect 0 means no control effect

From Colby's equation described above,

When the disease control effect of a combination of X with Y is found to be better than the expected effect (E) calculated from Colby's equation, the disease control effect of the combination is determined to be synergistic, not additive of these two components.

TABLE 7

| | Compounds-1 | Treated Conc. (ppm) | Compounds-2 | Treated Conc. (ppm) | Preventive value | E value |
|---|---|---|---|---|---|---|
| 1 | D-Tagatose | 50000 | — | — | 100.0 | — |
| 2 | | 10000 | — | — | 98.3 | — |
| 3 | | 5000 | — | — | 8.3 | — |
| 4 | | 1000 | — | — | 0.0 | — |
| 5 | D-Fructose | 5000 | — | — | 0.0 | — |
| 6 | D-Psicose | 5000 | — | — | 0.0 | — |
| 7 | D-Sorbose | 5000 | — | — | 0.0 | — |
| 9 | D-Mannose | 5000 | — | — | 0.0 | — |
| 10 | D-Tagatose | 5000 | D-Fructose | 5000 | 75.0 | 8.3 |
| | | | D-Psicose | 5000 | 76.7 | 8.3 |
| | | | D-Sorbose | 5000 | 55.0 | 8.3 |
| | | | D-Mannose | 5000 | 25.0 | 8.2 |
| 14 | Probenazole | 100 | | | 66.7 | — |
| 15 | Acibenzolar-S-Methyl | 50 | | | 95.0 | — |
| 16 | Metalaxyl | 300 | | | 100.0 | — |
| 17 | Untreated | | | | — | — |

As the result of this test, combinations of D-tagatose 0.5% with each of saccharides 0.5% were found to provide unexpectedly better disease control than expected from the calculated values from Colby's equation, thus demonstrating synergistic effect. The preventive values of the tests sprayed with combinations of D-tagatose solution 0.5% with D-fructose, D-psicose, D-sorbose or D-mannose were 75.0, 76.7, 55.0 and 25.0, respectively. As the expected effects (E) of the combinations calculated from Colby's equation were all 8.3, the combination of D-tagatose with each of these 4 saccharides proves to be unexpectedly and superiorly effective than each component alone.

EXAMPLE 8

This example shows the disease control test on cucumber powdery mildew (pot test: preventive effect).

Test plants (cucumber, variety: Sagami-hanpaku) were seeded and grown until the one true leaf stage. D-tagatose was diluted to 5% and 1% with distilled water and then 10ml of the dilution was sprayed on the test plant. Three days after spraying, a condia suspension of *Sphaerotheca fuligine* was inoculated by spraying on test plants. Seven days after inoculation the disease severity of the test plants was observed and the effectiveness of test sample was judged. Tests were carried out using two plants for each test set and the disease severity of the test plants was judged in accordance with the following criteria. The preventive value was calculated from the degree of disease severity as in Example 1.

TABLE 8

| | Compounds | Treated concentration (ppm) | Preventive value |
|---|---|---|---|
| 1 | D-Tagatose | 50000 | 87.5 |
| | | 10000 | 20.0 |
| 2 | D-Glucose | 50000 | 0.0 |
| | | 10000 | 0.0 |
| 3 | Iminoctadine albesilate(WP) | 300 | 98.3 |
| 4 | Untreated | | — |

The result of this test shows the preventive values of the tests sprayed with D-tagatose solution 5% and 1% were 87.5 and 20.0, respectively. D-Tagatose was effective enough against cucumber powdery mildew.

EXAMPLE 9

This example shows the disease control test on rice seedling blight (pot test: soil drench test).

Four germinated rice seeds (variety: Koshihikari) were sowed in a pot (5×5 cm), which contains infected soil with *Pythium glaminicola* (mycelium 100g/1L soil). The pot was drenched with 10ml of D-tagatose dilution and the seeds were covered with soil. After 2 weeks, the disease severity of the test plants per rice seedling in 25cm² was observed and the effectiveness of test sample was judged. Tests were carried out in duplicate and the preventive value was calculated from percentage of onset area.

TABLE 9

| Compounds | Treated concentration (ppm) | Preventive value |
|---|---|---|
| 1 D-Tagatose | 50000 | 96.2 |
|  | 10000 | 77.3 |
| 2 D-Glucose | 50000 | 4.5 |
|  | 10000 | 3.0 |
| 3 Hymexazol(SC) | 300 | 97.7 |
| 4 Untreated | — | — |

The result of this test shows the preventive values of the tests drenched with D-tagatose solution 5% and 1% were 96.2 and 77.3, respectively. D-Tagatose was effective enough against rice seedling blight.

EXAMPLE 10

This example shows the disease control test on wheat brown rust (field trial).

Test plants (variety: Nourin 61 gou) were sowed and grown until heading stage. D-Tagatose was diluted to 5% with distilled water and sprayed thoroughly on the plants two times every 8 days. Three days after the first spraying of the dilution, wheat leaves inoculated with wheat fusarium blight (*Puccinia recondita*) were kept in the test plants. The disease severity of the test plants was observed 21 days after last spraying and the effectiveness of test sample was judged. Tests were carried out in duplicate. One plot of each test was 5 m². The disease severity of the test plants was judged in accordance with the following criteria. The preventive value was calculated from the degree of disease severity.

[Disease Severity]
0 (No lesion)
1 Number of uredinium: 1-5
2 Number of uredinium: 6-12
3 Number of uredinium: 13-25
4 Number of uredinium: 25-50
5 Number of uredinium: 51-100
6 Number of uredinium: more than 100
[Degree of Disease Severity and Preventive Value]
Degree of disease severity=$100 \times \{(1n+2n+3n+4n+5n+6n)/6N\}$
N=number of leaves observed
n=number of leaves among N, which shows each disease severity
Preventive value=$100\{1-(n_1/N_1)\}$
$N_1$=Degree of disease severity of untreated plot, $n_1$=Degree of disease severity of the treated plot

TABLE 10

| Compounds | Treated con. (ppm) | N | | Leaves number(n) of each disease severity | | | | | | | D.D.S | P.V. |
|---|---|---|---|---|---|---|---|---|---|---|---|---|
| | | | | 0 | 1 | 2 | 3 | 4 | 5 | 6 | | |
| 1 D-Tagatose | 50000 | 1 | 100 | 76 | 22 | 0 | 2 | 0 | 0 | 0 | 4.7 | |
| | | 2 | 100 | 68 | 25 | 1 | 6 | 0 | 0 | 0 | 7.5 | |
| | | Av | | | | | | | | | 6.1 | 92.5 |
| 2 Tebuconazole | 200 | 1 | 100 | 100 | 0 | 0 | 0 | 0 | 0 | 0 | 0.0 | |
| | | 2 | 100 | 98 | 2 | 0 | 0 | 0 | 0 | 0 | 0.3 | |
| | | Av | | | | | | | | | 0.2 | 99.8 |
| 3 Untreated | | 1 | 100 | 0 | 28 | 16 | 31 | 5 | 8 | 12 | 47.5 | |
| | | 2 | 100 | 0 | 0 | 0 | 0 | 1 | 8 | 91 | 98.3 | |
| | | 3 | 100 | 0 | 0 | 0 | 2 | 0 | 5 | 93 | 98.2 | |
| | | Av | | | | | | | | | 81.3 | — |

D.D.S.: Degree of disease severity,
P.V.: Preventive value

The result of this test shows the preventive values of the tests sprayed with D-tagatose solution 5% was 92.5. D-Tagatose was effective enough against wheat *Fusarium* blight.

EXAMPLE 11

This example shows the disease control test on cabbage downy mildew (pot test: preventive effect).

Test plants (cabbage, variety: Shikidori) were seeded and grown until 4 leaves stage. D-Tagatose was diluted to 5% and 1% solution with distilled water and then 10ml of the dilution was sprayed on the test plant. Three days after spraying, a suspension containing condia of cucumber downy mildew (*Peronospora parasitica*) was inoculated by spraying on test plants. Seven days after inoculation the disease severity of the test plants was observed and the effectiveness of test sample was judged. Tests were carried out using two plants for each test set and the disease severity of test plants was judged in accordance with the following criteria. The preventive value was calculated from the degree of disease severity as in Example 1.

TABLE 11

| Compounds | Treated concentration (ppm) | Preventive value |
|---|---|---|
| 1 D-Tagatose | 50000 | 95.1 |
|  | 10000 | 90.1 |
| 2 D-Glucose | 50000 | 0.0 |
|  | 10000 | 0.0 |
| 3 Metalaxyl | 600 | 98.4 |
| 4 Untreated | — | — |

The result of this test shows the preventive values of the tests sprayed with D-tagatose solution 5% and 1% were 95.1 and 90.1%, respectively. D-Tagatose was effective enough against cabbage downy mildew.

EXAMPLE 12

This example shows the disease control test on vine downy mildew (field test).

Test plants (variety: kyoho) were grown until approximately 10 leaves. D-Tagatose was diluted to 5% and 1% with distilled water and sprayed thoroughly on the plants 4 times every 7 days. After the first spraying of the dilution, grape leaves were infected by spraying a sporangium suspension of *Plasmopara viticola* containing $1\times10^3$/ml. The disease severity of the test plants was observed 7 days after last spraying, and the effectiveness of test sample was judged. Tests were carried out in triplicate using half of the test plant per each test. The disease severity of the test plants was judged in accordance with the following criteria. The preventive value was calculated from the degree of disease severity.

[Disease Severity]
0 (No lesion)
1 (Lesion area was not more than 5% of the leaf area)
2 ((Lesion area was 5%-25% of the leaf area)
3 (Lesion area was 25%-50% of the leaf area)
4 (Lesion area was not less than 50% of the leaf area)
[Degree of Disease Severity and Preventive Value]
Degree of disease severity=$100\times\{(1n+2n+3n+4n)/4N\}$
N=number of leaves observed
n=number of leaves among N, which shows each disease severity
Preventive value=$100\{1-(n/N)\}$
N=Degree of disease severity of untreated plot, n=Degree of disease severity of the treated plot The result of this test shows the preventive values of the tests sprayed with D-tagatose solution 5% and 1% were 99.4 and 71.7, respectively. D-Tagatose was effective enough against grape downy mildew.

EXAMPLE 13

This example shows the disease control test on cucumber powdery mildew (field test).

Test plants (cucumber, variety: Ancor) were grown until approximately 10 leaves. D-Tagatose was diluted to 5% and 1% solution with distilled water and sprayed thoroughly on the plants 4 times every 7 days. After the first spraying of the dilution, the test plants were inoculated with condia of suspension of *Sphaerotheca fuliginea*. The disease severity of the test plants was observed 7 days after the last spraying, and the effectiveness of test sample was judged. Tests were carried out in triplicate using 8 plants per each test. The disease severity of the test plants was judged in accordance with the following criteria. The preventive value was calculated from the degree of disease severity.

[Disease Severity]
0 (No lesion)
1 (Lesion area was not more than 5% of the leaf area)
2 ((Lesion area was 5%-25% of the leaf area)
3 (Lesion area was 25%-50% of the leaf area)
4 (Lesion area was not less than 50% of the leaf area)
[Degree of Disease Severity and Preventive Value]
Degree of disease severity=$100\times\{(1n+2n+3n+4n)/4N\}$
N=number of leaves observed
n=number of leaves among N, which shows each disease severity
Preventive value=$100\{1-(n/N)\}$
N=Degree of disease severity of untreated plant, n=Degree of disease severity of the treated plant

TABLE 12

| | Compounds | Treated con. (ppm) | N | Disease severity 0 | 1 | 2 | 3 | 4 | n/N × 100 | D.D.S | P.V. |
|---|---|---|---|---|---|---|---|---|---|---|---|
| 1 | D-Tagatose | 50000 | 1 | 50 | 50 | 0 | 0 | 0 | 0 | 0.0 | 0.00 | 100.0 |
| | | | 2 | 50 | 50 | 0 | 0 | 0 | 0 | 0.0 | 0.00 | 100.0 |
| | | | 3 | 50 | 48 | 2 | 0 | 0 | 0 | 4.0 | 1.00 | 93.1 |
| | | | Av | | | | | | | 0.0 | 0.00 | 99.4 |
| 2 | D-Tagatose | 10000 | 1 | 50 | 37 | 8 | 2 | 2 | 1 | 26.0 | 11.00 | 78.7 |
| | | | 2 | 50 | 32 | 8 | 9 | 1 | 0 | 36.0 | 14.50 | 72.0 |
| | | | 3 | 50 | 34 | 4 | 5 | 5 | 2 | 32.0 | 18.50 | 64.3 |
| | | | Av | | | | | | | 31.0 | 12.75 | 71.7 |
| 3 | Cyazofamid (FL) | 94 | 1 | 50 | 46 | 4 | 0 | 0 | 0 | 8.0 | 2.00 | 96.1 |
| | | | 2 | 50 | 50 | 0 | 0 | 0 | 0 | 0.0 | 0.00 | 100.0 |
| | | | 3 | 50 | 45 | 4 | 1 | 0 | 0 | 10.0 | 3.00 | 94.2 |
| | | | Av | | | | | | | 4.0 | 1.00 | 96.8 |
| 4 | Untreated | | 1 | 50 | 21 | 8 | 6 | 10 | 5 | 58.0 | 35.00 | — |
| | | | 2 | 50 | 14 | 9 | 5 | 19 | 3 | 72.0 | 44.00 | — |
| | | | 3 | 50 | 4 | 7 | 11 | 20 | 8 | 92.0 | 60.50 | — |
| | | | 4 | 50 | 11 | 8 | 9 | 20 | 2 | 78.0 | 47.00 | — |
| | | | 5 | 50 | 5 | 14 | 7 | 14 | 10 | 90.0 | 55.00 | — |
| | | | 6 | 50 | 3 | 5 | 11 | 13 | 18 | 94.0 | 69.00 | — |
| | | | Av | | | | | | | 65.0 | 51.75. | — |

D.D.S.: Degree of disease severity,
P.V.: Preventive value

TABLE 13

| Compounds | Treated con. (ppm) | N | Disease severity 0 | 1 | 2 | 3 | 4 | n/N × 100 | D.D.S | P.V. |
|---|---|---|---|---|---|---|---|---|---|---|
| 1 D-Tagatose | 50000 | 1 50 | 48 | 2 | 0 | 0 | 0 | 4.0 | 1.00 | 99.0 |
|  |  | 2 50 | 47 | 3 | 0 | 0 | 0 | 6.0 | 1.50 | 98.4 |
|  |  | Av |  |  |  |  |  | 5.0 | 1.25 | 98.7 |
| 2 D-Tagatose | 10000 | 1 50 | 46 | 2 | 1 | 1 | 0 | 8.0 | 3.50 | 96.4 |
|  |  | 2 50 | 39 | 7 | 3 | 1 | 0 | 22.0 | 8.00 | 91.7 |
|  |  | Av |  |  |  |  |  | 15.0 | 5.75 | 94.0 |
| 4 Untreated |  | 1 50 | 0 | 0 | 1 | 8 | 41 | 100.0 | 95.00 | — |
|  |  | 2 50 | 0 | 0 | 1 | 3 | 46 | 100.0 | 97.50 | — |
|  |  | Av |  |  |  |  |  | 100.0 | 96.25. | — |

D.D.S.: Degree of disease severity,
P.V.: Preventive value

The result of this test shows the preventive values of the tests sprayed with D-tagatose solution 5% and 1% were 98.7 and 94.0, respectively. D-Tagatose was effective enough against cucumber powdery mildew.

EXAMPLE 14

This example shows the disease control test on cucumber downy mildew (pot test: preventive effect of a combination of D-tagatose with various fungicides).

Test plants (cucumber, variety: Sagami hanpaku) were seeded and grown until the one true leaf stage. D-Tagatose was diluted to 5000ppm and the fungicides were diluted to the concentrations listed in table 14, with distilled water. And then 10ml of the dilution was sprayed on the test plant. Three days after spraying of the solution, a sporangium suspension of *Pseudoperonospora cubensis* containing $1\times10^3$/ml were inoculated by spraying on test plants and then put for 16 hours in an inoculation chamber (20° C. to 23° C.) to promote disease. Seven days after inoculation the disease severity of the test plants was observed and the effectiveness of the test sample was judged. Tests were carried out using two plants for each test set and the disease severity of the test plants was judged in accordance with the following criteria. The preventive value was calculated from the degree of disease severity.

[Disease Severity]
0 (No lesion)
1 (Lesion area was not more than 40%)
2 ((Lesion area was 40%-80%)
3 (Lesion area was not less than 80%)
[Preventive Value]
Preventive value=100{1−(n/N)}
N=disease severity of untreated leaf, n=disease severity of the test leaf
Synergistic effect was determined by Colby's equation.

$$E=(X+Y)-(X*Y)/100$$

X is the observed percentage effect of the first active ingredient at the same use rate as in the mixture, and Y is the observed percentage effect of the second active ingredient at the same use rate as in the mixture.

E is the percentage effect of the mixture expected from additive contribution of the individual components.

E, X and Y: 100 means prefect disease control effect
0 means no disease control effect
From Colby's equation described above,
When the disease control effect of a combination of X with Y is found to be better than the expected effect (E) calculated from Colby's equation, the disease control effect of the combination is determined to be synergistic, not additive of these two components.

TABLE 14

| D-Tagatose + Compounds | Treated con. (ppm) | Preventive value | E value |
|---|---|---|---|
| D-Tagatose + azoxystrobin | 5000 + 10 | 83 | 70 |
| D-Tagatose + simeconazole | 5000 + 250 | 33 | 40 |
| D-Tagatose + penthiopyrad | 5000 + 50 | 33 | 40 |
| D-Tagatose + fluopicolide | 5000 + 10 | 100 | 90 |
| D-Tagatose + zoxamide | 5000 + 2 | 73 | 80 |
| D-Tagatose + mandipropamid | 5000 + 0.4 | 83 | 80 |
| D-Tagatose + metalaxyl | 5000 + 2 | 73 | 80 |
| D-Tagatose + benthiavalicarb-isopropyl | 5000 + 0.4 | 83 | 84 |
| D-Tagatose + cyazofamid | 5000 + 0.4 | 100 | 84 |
| D-Tagatose + propamocarb hydrochloride | 5000 + 250 | 93 | 80 |
| D-Tagatose + manzeb | 5000 + 10 | 90 | 94 |
| D-Tagatose + iminoctadine albesilate | 5000 + 250 | 73 | 64 |
| D-Tagatose + cyprodinil | 5000 + 250 | 33 | 40 |
| D-Tagatose + dimethomorph | 5000 + 10 | 73 | 80 |
| D-Tagatose + thiophanate-methyl | 5000 + 250 | 33 | 40 |
| D-Tagatose + fludioxonil | 5000 + 10 | 90 | 80 |
| D-Tagatose + cupric hydroxide | 5000 + 50 | 73 | 64 |
| D-Tagatose + chlorothalonil | 5000 + 50 | 100 | 90 |
| D-Tagatose + fosethyl | 5000 + 250 | 33 | 40 |
| D-Tagatose + hymexazol | 5000 + 250 | 33 | 40 |
| D-Tagatose + cymoxanil | 5000 + 50 | 67 | 60 |
| D-Tagatose + fluazinam | 5000 + 10 | 100 | 98 |
| D-Tagatose + fenamidone | 5000 + 2 | 97 | 60 |
| azoxystrobin | 10 | 50 | — |
| simeconazole | 250 | 0 | — |
| penthiopyrad | 50 | 0 | — |
| fluopicolide | 10 | 83 | — |
| zoxamide | 2 | 67 | — |
| mandipropamid | 0.4 | 67 | — |
| metalaxyl | 2 | 67 | — |
| benthiavalicarb-isopropyl | 0.4 | 73 | — |
| cyazofamid | 0.4 | 73 | — |
| propamocarb hydrochloride | 250 | 67 | — |
| manzeb | 10 | 90 | — |
| iminoctadine albesilate | 250 | 40 | — |
| cyprodinil | 250 | 0 | — |
| dimethomorph | 10 | 67 | — |
| thiophanate-methyl | 250 | 0 | — |
| fludioxonil | 10 | 57 | — |
| cupric hydroxide | 50 | 40 | — |
| chlorothalonil | 50 | 83 | — |
| fosethyl | 250 | 0 | — |
| hymexazol | 250 | 0 | — |
| cymoxanil | 50 | 33 | — |
| fluazinam | 10 | 97 | — |
| fenamidone | 2 | 33 | — |
| D-Tagatose | 10000 | 83 | — |
|  | 5000 | 40 | — |

In this experiment, the combinations of D-tagatose (5000 ppm) with the following chemical such as azoxystrobin (10 ppm), fluopicolide (10 ppm), mandipropamid (0.4 ppm), cyazofamid (0.4 ppm), propamocarb hydrochloride (250 ppm), iminoctadine albesilate (250 ppm), fludioxonil (10 ppm), cupric hydroxide (50 ppm), chlorothalonil (50 ppm), cymoxanil (50 ppm), fluazinam (10 ppm) and fenamidone (2 ppm) were found to be synergistically effective.

EXAMPLE 15

This example shows the disease control test on cucumber downy mildew (pot test: curative effect of a combination of D-tagatose with various fungicides).

Test plants (cucumber, variety: Sagami hanpaku) were seeded and grown until the one true leaf stage. And then, a sporangium suspension of *Pseudoperonospora cubensis* containing $1\times10^3$/ml were spraying for inoculation on the back side of the leaves of test plants and then put for 16 hours in an inoculation chamber (20° C. to 23° C.) to promote disease. For a curative test, the inoculated plants as described above were used.

D-Tagatose was diluted to 5000 ppm and the fungicides were diluted to the concentrations listed in table 15, with distilled water, and 10 ml of the dilution was sprayed. Seven days after inoculation the disease severity of the test plants was observed and the effectiveness of test sample was judged. The disease severity of the test plants was judged as in Example 14. The disease control value and the expected effect from Colby's equation were calculated as in Example 14.

TABLE 15

| D-Tagatose + Compounds | Treated con. (ppm) | Preventive value | E value |
| --- | --- | --- | --- |
| D-Tagatose + azoxystrobin | 5000 + 10 | 93 | 67 |
| D-Tagatose + simeconazole | 5000 + 250 | 50 | 33 |
| D-Tagatose + penthiopyrad | 5000 + 50 | 67 | 33 |
| D-Tagatose + fluopicolide | 5000 + 10 | 100 | 89 |
| D-Tagatose + zoxamide | 5000 + 2 | 100 | 56 |
| D-Tagatose + mandipropamid | 5000 + 0.4 | 90 | 60 |
| D-Tagatose + metalaxyl | 5000 + 2 | 100 | 56 |
| D-Tagatose + benthiavalicarb-isopropyl | 5000 + 0.4 | 100 | 56 |
| D-Tagatose + cyazofamid | 5000 + 0.4 | 100 | 33 |
| D-Tagatose + propamocarb hydrochloride | 5000 + 250 | 100 | 60 |
| D-Tagatose + manzeb | 5000 + 10 | 17 | 33 |
| D-Tagatose + iminoctadine albesilate | 5000 + 250 | 100 | 33 |
| D-Tagatose + cyprodinil | 5000 + 250 | 50 | 33 |
| D-Tagatose + dimethomorph | 5000 + 10 | 73 | 60 |
| D-Tagatose + thiophanate-methyl | 5000 + 250 | 17 | 33 |
| D-Tagatose + fludioxonil | 5000 + 10 | 17 | 33 |
| D-Tagatose + cupric hydroxide | 5000 + 50 | 17 | 33 |
| D-Tagatose + chlorothalonil | 5000 + 50 | 50 | 33 |
| D-Tagatose + fosethyl | 5000 + 250 | 67 | 33 |
| D-Tagatose + hymexazol | 5000 + 250 | 33 | 33 |
| D-Tagatose + cymoxanil | 5000 + 50 | 100 | 89 |
| D-Tagatose + fluazinam | 5000 + 10 | 50 | 33 |
| D-Tagatose + fenamidone | 5000 + 2 | 83 | 56 |
| azoxystrobin | 10 | 50 | — |
| simeconazole | 250 | 0 | — |
| penthiopyrad | 50 | 0 | — |
| fluopicolide | 10 | 83 | — |
| zoxamide | 2 | 33 | — |
| mandipropamid | 0.4 | 40 | — |
| metalaxyl | 2 | 33 | — |
| benthiavalicarb-isopropyl | 0.4 | 33 | — |
| cyazofamid | 0.4 | 0 | — |
| propamocarb hydrochloride | 250 | 40 | — |
| manzeb | 10 | 0 | — |
| iminoctadine albesilate | 250 | 0 | — |
| cyprodinil | 250 | 0 | — |
| dimethomorph | 10 | 40 | — |
| thiophanate-methyl | 250 | 0 | — |
| fludioxonil | 10 | 0 | — |
| cupric hydroxide | 50 | 0 | — |
| chlorothalonil | 50 | 0 | — |
| fosethyl | 250 | 0 | — |
| hymexazol | 250 | 0 | — |
| cymoxanil | 50 | 83 | — |
| fluazinam | 10 | 0 | — |
| fenamidone | 2 | 33 | — |
| D-Tagatose | 10000 | 73 | — |
|  | 5000 | 33 | — |

In this experiment, the combinations of D-tagatose (5000 ppm) with the following chemicals such as azoxystrobin (10 ppm), simeconazole (250 ppm), penthiopyrad (50 ppm), fluopicolide (10 ppm), zoxamide (2 ppm), mandipropamid (0.4 ppm), metalaxyl (2 ppm), benthiavalicarb (0.4 ppm), cyazofamid (0.4 ppm), propamocarb hydrochloride (250 ppm), iminoctadine albesilate (250 ppm), cyprodinil (250 ppm), dimethomorph (10 ppm), chlorothalonil (50 ppm), fosethyl (250 ppm), cymoxanil (50 ppm), fluazinam (10 ppm) and fenamidone (2 ppm) were found to be synergistically effective.

EXAMPLE 16

This example shows the disease control test on vine downy mildew (pot test; preventive effect of a combination of D-tagatose with various fungicides).

Test plants (variety: Neo Muscat) were seeded and grown until three leaves. D-Tagatose was diluted to 5000 ppm and the fungicides were diluted to the concentrations listed in table 16, with distilled water, and 10 ml of the dilution was sprayed on the plants. Three days after the spraying of the dilution, the plants were infected by spraying a sporangium suspension of *Plasmopara viticola* containing $1\times10^3$/ml and then put for 16 hours in an inoculation chamber (20° C. to 23° C.) to promote disease. The disease severity of the test plants was observed 7 days after inoculation, and the effectiveness of test sample was judged. The disease severity of the test plants was judged as in Example 14. The disease control value and the expected effect from Colby's equation were calculated as in Example 14.

TABLE 16

| D-Tagatose + Compounds | Treated con. (ppm) | Preventive value | E value |
| --- | --- | --- | --- |
| D-Tagatose + azoxystrobin | 5000 + 10 | 100 | 86 |
| D-Tagatose + simeconazole | 5000 + 250 | 40 | 17 |
| D-Tagatose + penthiopyrad | 5000 + 50 | 17 | 17 |
| D-Tagatose + fluopicolide | 5000 + 10 | 100 | 78 |
| D-Tagatose + zoxamide | 5000 + 2 | 93 | 86 |
| D-Tagatose + mandipropamid | 5000 + 0.4 | 100 | 78 |
| D-Tagatose + metalaxyl | 5000 + 2 | 67 | 58 |
| D-Tagatose + benthiavalicarb-isopropyl | 5000 + 0.4 | 67 | 58 |
| D-Tagatose + cyazofamid | 5000 + 0.4 | 83 | 58 |
| D-Tagatose + propamocarb hydrochloride | 5000 + 250 | 67 | 44 |
| D-Tagatose + manzeb | 5000 + 10 | 100 | 44 |
| D-Tagatose + iminoctadine albesilate | 5000 + 250 | 73 | 17 |
| D-Tagatose + cyprodinil | 5000 + 250 | 33 | 17 |
| D-Tagatose + dimethomorph | 5000 + 10 | 100 | 58 |
| D-Tagatose + thiophanate-methyl | 5000 + 250 | 33 | 17 |
| D-Tagatose + fludioxonil | 5000 + 10 | 50 | 44 |
| D-Tagatose + cupric hydroxide | 5000 + 50 | 83 | 17 |
| D-Tagatose + chlorothalonil | 5000 + 50 | 100 | 78 |
| D-Tagatose + fosethyl | 5000 + 250 | 67 | 17 |
| D-Tagatose + hymexazol | 5000 + 250 | 67 | 17 |
| D-Tagatose + cymoxanil | 5000 + 50 | 100 | 78 |
| D-Tagatose + fluazinam | 5000 + 10 | 97 | 86 |
| D-Tagatose + fenamidone | 5000 + 2 | 100 | 86 |
| azoxystrobin | 10 | 83 | — |

TABLE 16-continued

| D-Tagatose + Compounds | Treated con. (ppm) | Preventive value | E value |
|---|---|---|---|
| simeconazole | 250 | 0 | — |
| penthiopyrad | 50 | 0 | — |
| fluopicolide | 10 | 73 | — |
| zoxamide | 2 | 83 | — |
| mandipropamid | 0.4 | 73 | — |
| metalaxyl | 2 | 50 | — |
| benthiavalicarb-isopropyl | 0.4 | 50 | — |
| cyazofamid | 0.4 | 50 | — |
| propamocarb hydrochloride | 250 | 33 | — |
| manzeb | 10 | 33 | — |
| iminoctadine albesilate | 250 | 0 | — |
| cyprodinil | 250 | 0 | — |
| dimethomorph | 10 | 50 | — |
| thiophanate-methyl | 250 | 0 | — |
| fludioxonil | 10 | 33 | — |
| cupric hydroxide | 50 | 0 | — |
| chlorothalonil | 50 | 73 | — |
| fosethyl | 250 | 0 | — |
| hymexazol | 250 | 0 | — |
| cymoxanil | 50 | 73 | — |
| fluazinam | 10 | 83 | — |
| fenamidone | 2 | 83 | — |
| D-Tagatose | 10000 | 67 | — |
|  | 5000 | 17 | — |

In this experiment, the combinations of D-tagatose (5000 ppm) with the following chemicals such as azoxystrobin (10 ppm), simeconazole (250 ppm), fluopicolide (10 ppm), zoxamide (2 ppm), mandipropamid (0.4 ppm), metalaxyl (2 ppm), benthiavalicarb-isopropyl (0.4 ppm), cyazofamid (0.4 ppm), propamocarb hydrochloride (250 ppm), manzeb (10 ppm), iminoctadine albesilate (250 ppm), cyprodinil (250 ppm), dimethomorph (10 ppm), thiophanate-methyl (250 ppm), fludioxonil (10 ppm), cupric hydroxide (50 ppm), chlorothalonil (50 ppm), fosethyl (250 ppm), hymexazol (250 ppm), cymoxanil (50 ppm), fluazinam (10 ppm) and fenamidone (2 ppm) were found to be synergistically effective.

EXAMPLE 17

This example shows the disease control test on tomato late bright (pot test: preventive effect of a combination of D-tagatose with various fungicides).

Test plants (tomato, variety: Ogata-fukujyu) were seeded and grown until the three leaf stage.

D-Tagatose was diluted to 5000ppm and the fungicides were diluted to the concentrations listed in table 17, with distilled water, and 10 ml of the dilution was sprayed on the plants. Three days after spraying the solution, a sporangium suspension of *Phytophthora infestans* containing $1 \times 10^3$/ml were inoculated by spraying on test plants and then put for 16 hours in an inoculation chamber (20° C. to 23° C.) to promote disease. Seven days after inoculation the disease severity of the test plants was observed and the effectiveness of test sample was judged. The disease severity of the test plants was judged as in Example 14. The disease control value and the expected effect from Colby's equation were calculated as in Example 14.

TABLE 17

| D-Tagatose + Compounds | Treated con. (ppm) | Preventive value | E value |
|---|---|---|---|
| D-Tagatose + azoxystrobin | 5000 + 10 | 100 | 83 |
| D-Tagatose + simeconazole | 5000 + 250 | 67 | 0 |
| D-Tagatose + penthiopyrad | 5000 + 50 | 67 | 0 |

TABLE 17-continued

| D-Tagatose + Compounds | Treated con. (ppm) | Preventive value | E value |
|---|---|---|---|
| D-Tagatose + fluopicolide | 5000 + 10 | 100 | 83 |
| D-Tagatose + zoxamide | 5000 + 2 | 60 | 50 |
| D-Tagatose + mandipropamid | 5000 + 0.4 | 93 | 73 |
| D-Tagatose + metalaxyl | 5000 + 2 | 83 | 67 |
| D-Tagatose + benthiavalicarb-isopropyl | 5000 + 0.4 | 83 | 73 |
| D-Tagatose + cyazofamid | 5000 + 0.4 | 100 | 17 |
| D-Tagatose + propamocarb hydrochloride | 5000 + 250 | 73 | 67 |
| D-Tagatose + manzeb | 5000 + 10 | 100 | 67 |
| D-Tagatose + iminoctadine albesilate | 5000 + 250 | 33 | 0 |
| D-Tagatose + cyprodinil | 5000 + 250 | 33 | 0 |
| D-Tagatose + dimethomorph | 5000 + 10 | 100 | 73 |
| D-Tagatose + thiophanate-methyl | 5000 + 250 | 40 | 0 |
| D-Tagatose + fludioxonil | 5000 + 10 | 40 | 0 |
| D-Tagatose + cupric hydroxide | 5000 + 50 | 100 | 50 |
| D-Tagatose + chlorothalonil | 5000 + 50 | 100 | 83 |
| D-Tagatose + fosethyl | 5000 + 250 | 40 | 33 |
| D-Tagatose + hymexazol | 5000 + 250 | 17 | 0 |
| D-Tagatose + cymoxanil | 5000 + 50 | 100 | 83 |
| D-Tagatose + fluazinam | 5000 + 10 | 100 | 83 |
| D-Tagatose + fenamidone | 5000 + 2 | 100 | 83 |
| azoxystrobin | 10 | 83 | — |
| simeconazole | 250 | 0 | — |
| penthiopyrad | 50 | 0 | — |
| fluopicolide | 10 | 83 | — |
| zoxamide | 2 | 50 | — |
| mandipropamid | 0.4 | 73 | — |
| metalaxyl | 2 | 67 | — |
| benthiavalicarb-isopropyl | 0.4 | 73 | — |
| cyazofamid | 0.4 | 17 | — |
| propamocarb hydrochloride | 250 | 67 | — |
| manzeb | 10 | 67 | — |
| iminoctadine albesilate | 250 | 0 | — |
| cyprodinil | 250 | 0 | — |
| dimethomorph | 10 | 73 | — |
| thiophanate-methyl | 250 | 0 | — |
| fludioxonil | 10 | 0 | — |
| cupric hydroxide | 50 | 50 | — |
| chlorothalonil | 50 | 83 | — |
| fosethyl | 250 | 33 | — |
| hymexazol | 250 | 0 | — |
| cymoxanil | 50 | 83 | — |
| fluazinam | 10 | 83 | — |
| fenamidone | 2 | 83 | — |
| D-Tagatose | 10000 | 40 | — |
|  | 5000 | 0 | — |

In this experiment, the combinations of D-tagatose (5000 ppm) with the following chemical such as azoxystrobin (10 ppm), simeconazole (250 ppm), penthiopyrad (50 ppm), fluopicolide (10 ppm), zoxamide (2 ppm), mandipropamid (0.4 ppm), metalaxyl (2 ppm), benthiavalicarb-isopropyl (0.4 ppm), cyazofamid (0.4 ppm), propamocarb hydrochloride (250 ppm), manzeb (10 ppm), iminoctadine albesilate (250 ppm), cyprodinil (250 ppm), dimethomorph (10 ppm), thiophanate-methyl (250 ppm), fludioxonil (10 ppm), cupric hydroxide (50 ppm), chlorothalonil (50 ppm), fosethyl (250 ppm), hymexazol (250 ppm), cymoxanil (50 ppm), fluazinam (10 ppm) and fenamidone (2 ppm) were found to be synergistically effective.

EXAMPLE 18

This example shows the disease control test on cucumber damping-off (pot test: soil drench test of a combination of D-tagatose with various fungicides).

Five seeds of test plants (cucumber, variety: Sagami hanpaku) were sowed in a pot (5×5 cm), which contains infested soil with *Pythium aphanidermatum* (mycelium 100 g/1 L soil) and was covered with soil. D-Tagatose was diluted to 5000ppm and the fungicides were diluted to the concentrations listed in table 18, with distilled water. The pot was drenched with 10 ml of the dilution. After 2 weeks, the disease severity of the test plants was observed and the effectiveness of test sample was judged. Tests were carried out in triplicate using 5 plants for each test set and the preventive value was calculated from the germination rate.

The disease severity of the test plants was judged, and the disease control value and the expected effect from Colby's equation were calculated as in Example 14.

TABLE 18

| D-Tagatose + Compounds | Treated con. (ppm) | Preventive value | E value |
|---|---|---|---|
| D-Tagatose + azoxystrobin | 5000 + 50 | 100 | 67 |
| D-Tagatose + simeconazole | 5000 + 250 | 0 | 33 |
| D-Tagatose + penthiopyrad | 5000 + 250 | 50 | 33 |
| D-Tagatose + fluopicolide | 5000 + 250 | 100 | 89 |
| D-Tagatose + zoxamide | 5000 + 250 | 33 | 33 |
| D-Tagatose + metalaxyl | 5000 + 2 | 100 | 89 |
| D-Tagatose + benthiavalicarb-isopropyl | 5000 + 250 | 50 | 33 |
| D-Tagatose + cyazofamid | 5000 + 50 | 100 | 89 |
| D-Tagatose + amisulbrom | 5000 + 50 | 100 | 89 |
| D-Tagatose + propamocarb hydrochloride | 5000 + 250 | 100 | 33 |
| D-Tagatose + cyprodinil | 5000 + 250 | 50 | 33 |
| D-Tagatose + dimethomorph | 5000 + 250 | 100 | 33 |
| D-Tagatose + thiophanate-methyl | 5000 + 250 | 50 | 33 |
| D-Tagatose + fludioxonil | 5000 + 250 | 33 | 33 |
| D-Tagatose + fosethyl | 5000 + 250 | 100 | 33 |
| D-Tagatose + hymexazol | 5000 + 50 | 100 | 78 |
| D-Tagatose + cymoxanil | 5000 + 250 | 100 | 44 |
| D-Tagatose + fenamidone | 5000 + 10 | 100 | 67 |
| azoxystrobin | 50 | 50 | — |
| simeconazole | 250 | 0 | — |
| penthiopyrad | 250 | 0 | — |
| fluopicolide | 250 | 83 | — |
| zoxamide | 250 | 0 | — |
| metalaxyl | 5 | 83 | — |
| benthiavalicarb-isopropyl | 250 | 0 | — |
| cyazofamid | 50 | 83 | — |
| amisulbrom | 50 | 83 | — |
| propamocarb hydrochloride | 250 | 0 | — |
| cyprodinil | 250 | 0 | — |
| dimethomorph | 250 | 0 | — |
| thiophanate-methyl | 250 | 0 | — |
| fludioxonil | 250 | 0 | — |
| fosethyl | 250 | 0 | — |
| hymexazol | 50 | 67 | — |
| cymoxanil | 250 | 17 | — |
| fenamidone | 10 | 50 | — |
| D-Tagatose | 10000 | 83 | — |
|  | 5000 | 33 | — |

In this experiment, the combinations of D-tagatose (5000 ppm) with the following chemical such as azoxystrobin (50 ppm), penthiopyrad (250 ppm), fluopicolide (250 ppm), metalaxyl (2 ppm), benthiavalicarb-isopropyl (250 ppm), cyazofamid (50 ppm), amisulbrom (50 ppm), propamocarb hydrochloride (250 ppm), cyprodinil (250 ppm), dimethomorph (250 ppm), thiophanate-methyl (250 ppm), fosethyl (250 ppm), hymexazol (50 ppm), cymoxanil (250 ppm) and fenamidone (10 ppm) were found to be synergistically effective.

EXAMPLE 19

This example shows the disease control test on wheat brown rust (pot test, preventive effect of a combination of D-tagatose with various fungicides).

Test plants (variety: Nourin 61 gou) were sowed and grown until two leaves stage.

D-Tagatose and fungicide were diluted to 10000ppm and the concentration listed in table 19, respectively, with distilled water, and 10 ml of the dilution was sprayed thoroughly on the plants. Three days after the spraying of the dilution, the plants were inoculated with *Puccinia recondita* containing $1 \times 10^3$/ml and then put for 16 hours in an inoculation chamber (20° C. to 23° C.) to promote disease. Seven days after inoculation the disease severity of the test plants was observed and the effectiveness of test sample was judged. The disease severity of the test plants was judged as in Example 14. The disease control value and the expected effect from Colby's equation were calculated as in Example 14.

TABLE 19

| D-Tagatose + Compounds | Treated con. (ppm) | Preventive value | E value |
|---|---|---|---|
| D-Tagatose + azoxystrobin | 10000 + 2 | 100 | 86 |
| D-Tagatose + simeconazole | 10000 + 10 | 90 | 72 |
| D-Tagatose + tebuconazole | 10000 + 0.4 | 83 | 58 |
| D-Tagatose + triflumizole | 10000 + 2 | 73 | 50 |
| D-Tagatose + boscalid | 10000 + 2 | 73 | 72 |
| D-Tagatose + penthiopyrad | 10000 + 0.4 | 73 | 72 |
| D-Tagatose + metalaxyl | 10000 + 250 | 17 | 17 |
| D-Tagatose + benthiavalicarb-isopropyl | 10000 + 250 | 17 | 17 |
| D-Tagatose + cyazofamid | 10000 + 250 | 17 | 17 |
| D-Tagatose + manzeb | 10000 + 50 | 100 | 86 |
| D-Tagatose + iprodione | 10000 + 250 | 93 | 44 |
| D-Tagatose + iminoctadine albesilate | 10000 + 250 | 93 | 50 |
| D-Tagatose + cyprodinil | 10000 + 250 | 100 | 72 |
| D-Tagatose + thiophanate-methyl | 10000 + 10 | 50 | 50 |
| D-Tagatose + fludioxonil | 10000 + 50 | 40 | 31 |
| D-Tagatose + polyoxin | 10000 + 50 | 40 | 22 |
| D-Tagatose + chlorothalonil | 10000 + 50 | 100 | 86 |
| D-Tagatose + fosethyl | 10000 + 250 | 17 | 17 |
| D-Tagatose + quinoxyfen | 10000 + 250 | 17 | 17 |
| D-Tagatose + hymexazol | 10000 + 250 | 17 | 17 |
| D-Tagatose + fluazinam | 10000 + 50 | 100 | 86 |
| azoxystrobin | 2 | 83 | — |
| simeconazole | 10 | 67 | — |
| tebuconazole | 0.4 | 50 | — |
| triflumizole | 2 | 40 | — |
| boscalid | 2 | 67 | — |
| penthiopyrad | 0.4 | 67 | — |
| metalaxyl | 250 | 0 | — |
| benthiavalicarb-isopropyl | 250 | 0 | — |
| cyazofamid | 250 | 0 | — |
| manzeb | 50 | 83 | — |
| iprodione | 250 | 33 | — |
| iminoctadine albesilate | 250 | 40 | — |
| cyprodinil | 250 | 67 | — |
| thiophanate-methyl | 10 | 40 | — |
| fludioxonil | 50 | 17 | — |
| polyoxin | 50 | 7 | — |
| chlorothalonil | 50 | 83 | — |
| fosethyl | 250 | 0 | — |
| quinoxyfen | 250 | 0 | — |
| hymexazol | 250 | 0 | — |
| fluazinam | 50 | 83 | — |
| D-Tagatose | 50000 | 50 | — |
|  | 10000 | 17 | — |

In this experiment, the combinations of D-tagatose (10000 ppm) with the following chemicals such as azoxystrobin (2 ppm), simeconazole (10 ppm), tebuconazole (0.4 ppm), triflumizole (2 ppm), boscalid (2 ppm), penthiopyrad (0.4 ppm), manzeb (50 ppm), iprodion (250 ppm), iminoctadine albesilate (250 ppm), cyprodinil (250 ppm), fludioxonil (50 ppm), polyoxin (50 ppm), chlorothalonil (50 ppm) and luazinam (50 ppm) were found to be synergistically effective.

EXAMPLE 20

This example shows the disease control test on cucumber powdery mildew (pot test: preventive effect of a combination of D-tagatose with various fungicides).

Test plants (cucumber, variety: Sagami hanpaku) were seeded and grown until the one true leaf stage. D-Tagatose and fungicide were diluted to 5000 ppm and the concentrations listed in table 20, respectively, with distilled water and 10 ml of the dilution was sprayed thoroughly on the plants. Three days after spraying, a condia suspension containing of *Sphaerotheca fuliginea* were inoculated by spraying on test plants.

Seven days after inoculation the disease severity of the test plants was observed and the effectiveness of test sample was judged. The disease severity of the test plants was judged as in Example 14. The disease control value and the expected effect from Colby's equation were calculated as in Example 14.

TABLE 20

| D-Tagatose + Compounds | Treated con. (ppm) | Preventive value | E value |
|---|---|---|---|
| D-Tagatose + azoxystrobin | 5000 + 0.4 | 83 | 80 |
| D-Tagatose + simeconazole | 5000 + 0.4 | 100 | 90 |
| D-Tagatose + tebuconazole | 5000 + 0.4 | 100 | 84 |
| D-Tagatose + triflumizole | 5000 + 0.4 | 100 | 98 |
| D-Tagatose + boscalid | 5000 + 0.4 | 67 | 80 |
| D-Tagatose + penthiopyrad | 5000 + 0.4 | 67 | 70 |
| D-Tagatose + cyflufenamid | 5000 + 0.4 | 93 | 70 |
| D-Tagatose + metalaxyl | 5000 + 250 | 50 | 40 |
| D-Tagatose + benthiavalicarb-isopropyl | 5000 + 250 | 33 | 40 |
| D-Tagatose + cyazofamid | 5000 + 250 | 67 | 40 |
| D-Tagatose + manzeb | 5000 + 50 | 60 | 70 |
| D-Tagatose + iprodione | 5000 + 250 | 67 | 60 |
| D-Tagatose + iminoctadine albesilate | 5000 + 50 | 100 | 90 |
| D-Tagatose + cyprodinil | 5000 + 10 | 83 | 80 |
| D-Tagatose + thiophanate-methyl | 5000 + 10 | 100 | 90 |
| D-Tagatose + fludioxonil | 5000 + 250 | 97 | 84 |
| D-Tagatose + polyoxin | 5000 + 50 | 83 | 90 |
| D-Tagatose + chlorothalonil | 5000 + 50 | 73 | 70 |
| D-Tagatose + fosethyl | 5000 + 250 | 83 | 50 |
| D-Tagatose + quinoxyfen | 5000 + 2 | 100 | 90 |
| D-Tagatose + hymexazol | 5000 + 250 | 33 | 40 |
| D-Tagatose + fluazinam | 5000 + 250 | 100 | 90 |
| azoxystrobin | 0.4 | 67 | — |
| simeconazole | 0.4 | 83 | — |
| tebuconazole | 0.4 | 73 | — |
| triflumizole | 0.4 | 97 | — |
| boscalid | 0.4 | 67 | — |
| penthiopyrad | 0.4 | 50 | — |
| cyflufenamid | 0.4 | 50 | — |
| metalaxyl | 250 | 0 | — |
| benthiavalicarb-isopropyl | 250 | 0 | — |
| cyazofamid | 250 | 0 | — |
| manzeb | 50 | 50 | — |
| iprodione | 250 | 33 | — |
| iminoctadine albesilate | 50 | 83 | — |
| cyprodinil | 10 | 67 | — |
| thiophanate-methyl | 10 | 83 | — |
| fludioxonil | 250 | 73 | — |
| polyoxin | 50 | 83 | — |
| chlorothalonil | 50 | 50 | — |
| fosethyl | 250 | 17 | — |
| quinoxyfen | 2 | 83 | — |
| hymexazol | 250 | 0 | — |
| fluazinam | 250 | 83 | — |
| D-Tagatose | 10000 | 93 | — |
|  | 5000 | 40 | — |

In this experiment, the combinations of D-tagatose (5000 ppm) with the following chemicals such as azoxystrobin (0.4 ppm), simeconazole (0.4 ppm), tebuconazole (0.4 ppm), triflumizole (0.4 ppm), cyflufenamid (0.4 ppm), metalaxyl (250 ppm), cyazofamid (250 ppm), iprodion (250 ppm), iminoctadine albesilate (50 ppm), cyprodinil (10 ppm), thiophanate-methyl (10 ppm), fludioxonil (250 ppm), chlorothalonil (50 ppm), fosethyl (250 ppm), quinoxyfen (2 ppm) and fluazinam (250 ppm) were found to be synergistically effective.

EXAMPLE 21

This example shows the disease control test on barley powdery mildew (pot test: preventive effect of a combination of D-tagatose with various fungicides). Test plants (barley, variety: Akashinriki) were seeded and grown until the one leaf stage. D-tagatose and fungicide were diluted to 5000ppm and the concentrations listed in table 21, respectively, with distilled water and 10ml of the dilution was sprayed thoroughly on the plants. Three days after spraying, a condia suspension of *Erysiphe graminis* f.sp. *hordei* was inoculated by spraying on test plants. 7 days after inoculation the disease severity of the test plants was observed and the effectiveness of test sample was judged. The disease severity of the test plants was judged as in Example 14. The disease control value and the expected effect from Colby's equation were calculated as in Example 14.

TABLE 21

| D-Tagatose + Compounds | Treated con. (ppm) | Preventive value | E value |
|---|---|---|---|
| D-Tagatose + azoxystrobin | 5000 + 0.4 | 100 | 75 |
| D-Tagatose + simeconazole | 5000 + 0.4 | 97 | 75 |
| D-Tagatose + tebuconazole | 5000 + 0.4 | 100 | 83 |
| D-Tagatose + triflumizole | 5000 + 0.4 | 100 | 75 |
| D-Tagatose + boscalid | 5000 + 0.4 | 50 | 58 |
| D-Tagatose + penthiopyrad | 5000 + 0.4 | 73 | 83 |
| D-Tagatose + cyflufenamid | 5000 + 0.4 | 73 | 83 |
| D-Tagatose + metalaxyl | 5000 + 250 | 73 | 50 |
| D-Tagatose + benthiavalicarb-isopropyl | 5000 + 250 | 17 | 50 |
| D-Tagatose + cyazofamid | 5000 + 250 | 17 | 50 |
| D-Tagatose + manzeb | 5000 + 50 | 40 | 70 |
| D-Tagatose + iprodione | 5000 + 250 | 40 | 58 |
| D-Tagatose + iminoctadine albesilate | 5000 + 50 | 33 | 58 |
| D-Tagatose + cyprodinil | 5000 + 10 | 100 | 58 |
| D-Tagatose + thiophanate-methyl | 5000 + 10 | 100 | 92 |
| D-Tagatose + fludioxonil | 5000 + 250 | 83 | 87 |
| D-Tagatose + polyoxin | 5000 + 50 | 50 | 83 |
| D-Tagatose + chlorothalonil | 5000 + 50 | 83 | 67 |
| D-Tagatose + fosethyl | 5000 + 250 | 50 | 58 |
| D-Tagatose + quinoxyfen | 5000 + 2 | 100 | 97 |
| D-Tagatose + hymexazol | 5000 + 250 | 40 | 50 |
| D-Tagatose + fluazinam | 5000 + 250 | 100 | 92 |
| azoxystrobin | 0.4 | 50 | — |
| simeconazole | 0.4 | 50 | — |
| tebuconazole | 0.4 | 67 | — |
| triflumizole | 0.4 | 50 | — |
| boscalid | 0.4 | 17 | — |
| penthiopyrad | 0.4 | 67 | — |
| cyflufenamid | 0.4 | 67 | — |
| metalaxyl | 250 | 0 | — |
| benthiavalicarb-isopropyl | 250 | 0 | — |
| cyazofamid | 250 | 0 | — |
| manzeb | 50 | 40 | — |
| iprodione | 250 | 17 | — |
| iminoctadine albesilate | 50 | 17 | — |
| cyprodinil | 10 | 17 | — |
| thiophanate-methyl | 10 | 83 | — |
| fludioxonil | 250 | 73 | — |
| polyoxin | 50 | 67 | — |
| chlorothalonil | 50 | 33 | — |
| fosethyl | 250 | 17 | — |
| quinoxyfen | 2 | 93 | — |
| hymexazol | 250 | 0 | — |
| fluazinam | 250 | 83 | — |
| D-Tagatose | 10000 | 73 | — |
|  | 5000 | 50 | — |

In this experiment, the combinations of D-tagatose (5000 ppm) with the following chemical such as azoxystrobin (0.4 ppm), simeconazole (0.4 ppm), tebuconazole (0.4 ppm), triflumizole (0.4 ppm), metalaxyl (250 ppm), cyprodinil (10 ppm), thiophanate-methyl (10 ppm), chlorothalonil (50 ppm), quinoxyfen (2 ppm) and fluazinam (250 ppm) were found to be synergistically effective.

EXAMPLE 22

This example shows the disease control test on rice blast (pot test: preventive effect of a combination of D-tagatose with various fungicides).

Test plants (rice, variety: Sachikaze) were seeded and grown until the one leaf stage. D-Tagatose and fungicide were diluted to 10000ppm and the concentrations listed in table 22, respectively, with distilled water and 10 ml of the dilution was sprayed thoroughly on the plants. Three days after spraying, a condia suspension of *Pyricularia oryze* was inoculated by spraying on test plants. Seven days after inoculation the disease severity of the test plants was observed and the effectiveness of test sample was judged. The disease severity of the test plants was judged as in Example 14. The disease control value and the expected effect from Colby's equation were calculated as in Example 14.

TABLE 22

| D-Tagatose + Compounds | Treated con. (ppm) | Preventive value | E value |
|---|---|---|---|
| D-Tagatose + azoxystrobin | 10000 + 10 | 100 | 83 |
| D-Tagatose + simeconazole | 10000 + 250 | 100 | 73 |
| D-Tagatose + penthiopyrad | 10000 + 50 | 73 | 40 |
| D-Tagatose + fluopicolide | 10000 + 250 | 33 | 0 |
| D-Tagatose + zoxamide | 10000 + 250 | 17 | 0 |
| D-Tagatose + cyazofamid | 10000 + 250 | 17 | 0 |
| D-Tagatose + iprodione | 10000 + 250 | 50 | 0 |
| D-Tagatose + iminoctadine albesilate | 10000 + 250 | 83 | 50 |
| D-Tagatose + cyprodinil | 10000 + 250 | 97 | 73 |
| D-Tagatose + thiophanate-methyl | 10000 + 250 | 97 | 83 |
| D-Tagatose + fludioxonil | 10000 + 50 | 100 | 83 |
| D-Tagatose + validamycin | 10000 + 10 | 73 | 50 |
| D-Tagatose + kasugamycin | 10000 + 10 | 100 | 73 |
| D-Tagatose + polyoxin | 10000 + 50 | 17 | 0 |
| D-Tagatose + fthalide | 10000 + 10 | 67 | 50 |
| D-Tagatose + hymexazol | 10000 + 250 | 40 | 33 |
| D-Tagatose + tricyclazole | 10000 + 10 | 60 | 50 |
| D-Tagatose + fluazinam | 10000 + 10 | 67 | 50 |
| azoxystrobin | 10 | 83 | — |
| simeconazole | 250 | 73 | — |
| penthiopyrad | 50 | 40 | — |
| fluopicolide | 250 | 0 | — |
| zoxamide | 250 | 0 | — |
| cyazofamid | 250 | 0 | — |
| iprodione | 250 | 0 | — |
| iminoctadine albesilate | 250 | 50 | — |
| cyprodinil | 250 | 73 | — |
| thiophanate-methyl | 250 | 83 | — |
| fludioxonil | 50 | 83 | — |
| validamycin | 10 | 50 | — |
| kasugamycin | 10 | 73 | — |
| polyoxin | 50 | 0 | — |
| fthalide | 10 | 50 | — |
| hymexazol | 250 | 33 | — |
| tricyclazole | 10 | 50 | — |
| fluazinam | 10 | 50 | — |
| D-Tagatose | 50000 | 50 | — |
|  | 10000 | 0 | — |

In this experiment, the combinations of D-tagatose (5 000 ppm) with the following chemical such as azoxystrobin (50 ppm), simeconazole (250 ppm), penthiopyrad (50 ppm), fluopicolide (250 ppm), zoxamide (250 ppm), cyazofamid (250 ppm), iprodione (250 ppm), iminoctadine albesilate (250 ppm), cyprodinil (250 ppm), thiophanate-methyl (250 ppm), fludioxonil (50 ppm), validamycin (10 ppm), kasugamycin (10 ppm), polyoxin (50 ppm), fthalide (10 ppm), hymexazol (250 ppm), tricyclazole (10 ppm) and ferimuzon (10 ppm) were found to be synergistically effective.

EXAMPLE 23

This example shows the disease control test on tomato gray mold (pot test: preventive effect of a combination of D-tagatose with various fungicides).

Test plants (tomato, variety: Ogata-fukujyu) were seeded and grown until the three leaf stage. D-Tagatose and fungicide were diluted to 10000 ppm and the concentrations liste in table 23, respectively, with distilled water and 10 ml of the dilution was sprayed on the plants. Three days after spraying the solution, condia suspension of *Botrytis cinerea* were inoculated by spraying on test plants and then put for 16 hours in an inoculation chamber (20° C. to 23° C.) to promote disease. Seven days after inoculation, the disease severity of the test plants was observed and the effectiveness of test sample was judged. The disease severity of the test plants was judged as in Example 14. The disease control value and the expected effect from Colby's equation were calculated as in Example 14.

TABLE 23

| D-Tagatose + Compounds | Treated con. (ppm) | Preventive value | E value |
|---|---|---|---|
| D-Tagatose + azoxystrobin | 10000 + 50 | 67 | 50 |
| D-Tagatose + simeconazole | 10000 + 50 | 50 | 33 |
| D-Tagatose + tebuconazole | 10000 + 10 | 50 | 33 |
| D-Tagatose + triflumizole | 10000 + 50 | 83 | 67 |
| D-Tagatose + boscalid | 10000 + 10 | 73 | 67 |
| D-Tagatose + penthiopyrad | 10000 + 10 | 73 | 67 |
| D-Tagatose + metalaxyl | 10000 + 250 | 17 | 0 |
| D-Tagatose + benthiavalicarb-isopropyl | 10000 + 250 | 0 | 0 |
| D-Tagatose + cyazofamid | 10000 + 250 | 0 | 0 |
| D-Tagatose + manzeb | 10000 + 50 | 40 | 40 |
| D-Tagatose + iprodione | 10000 + 2 | 50 | 40 |
| D-Tagatose + iminoctadine albesilate | 10000 + 10 | 83 | 67 |
| D-Tagatose + cyprodinil | 10000 + 10 | 93 | 73 |
| D-Tagatose + thiophanate-methyl | 10000 + 50 | 93 | 83 |
| D-Tagatose + fludioxonil | 10000 + 2 | 83 | 67 |
| D-Tagatose + polyoxin | 10000 + 50 | 83 | 73 |
| D-Tagatose + chlorothalonil | 10000 + 50 | 73 | 67 |
| D-Tagatose + quinoxyfen | 10000 + 250 | 0 | 0 |
| D-Tagatose + hymexazol | 10000 + 250 | 0 | 0 |
| D-Tagatose + fluazinam | 10000 + 50 | 27 | 67 |
| azoxystrobin | 50 | 50 | — |
| simeconazole | 50 | 33 | — |
| tebuconazole | 10 | 33 | — |
| triflumizole | 50 | 67 | — |
| boscalid | 10 | 67 | — |
| penthiopyrad | 10 | 67 | — |
| metalaxyl | 250 | 0 | — |
| benthiavalicarb-isopropyl | 250 | 0 | — |
| cyazofamid | 250 | 0 | — |
| manzeb | 50 | 40 | — |
| iprodione | 2 | 40 | — |
| iminoctadine albesilate | 10 | 67 | — |
| cyprodinil | 10 | 73 | — |
| thiophanate-methyl | 50 | 83 | — |
| fludioxonil | 2 | 67 | — |
| polyoxin | 50 | 73 | — |
| chlorothalonil | 50 | 67 | — |
| quinoxyfen | 250 | 0 | — |
| hymexazol | 250 | 0 | — |
| fluazinam | 50 | 67 | — |
| D-Tagatose | 50000 | 17 | — |
|  | 10000 | 0 | — |

In this experiment, the combinations of D-tagatose (5 000ppm) with the following chemical such as azoxystrobin (50ppm), simeconazole (50ppm), tebuconazole (10ppm), triflumizole (50ppm), boscalid (10ppm), penthiopyrad (10ppm), metalaxyl (250ppm), iprodione (2ppm), iminoctadine albesilate (10ppm), cyprodinil (10ppm), thiophanate-methyl (50ppm), fludioxonil (2ppm), polyoxin (50ppm) and chlorothalonil (50ppm) were found to be synergistically effective.

As is clear from the above examples, D-tagatose was shown to be effective in controlling various plant diseases. And the combination or the tank-mixing of D-tagatose with one or more substances selected among saccharides other than D-tagatose, or fungicidal and/or moldicidal materials, is able to show unexpected synergistic control efficacy against various plant diseases. As the mode of action of D-tagatose is different from those of existing fungicides, the combination or the tank-mixing of D-tagatose with existing fungicides is assumed to be effective without losing their additive effects of both components. The synergistic or additive combination or tank-mixing of D-tagatose with existing fungicides is able to contribute reducing the application dosage of existing fungicides which may cause hazard to human being and the environment, without causing any phytotoxicity.

Conventional fungicides used in Examples of this invention are representative compounds of each group, and other compounds having the same mode of action as the compounds used in the examples of this invention are expected to show similar synergistic effect with combination of D-tagatose.

For example, 11 compounds belonging to group (1) are respiration inhibitors targeting on mitochondrial complex III (QoI) and they show similar synergistic effect as azoxystrobin, one of representative compound of this group does.

Fenamidone, which does not belong to this group (1), acts similarly as the compounds belonging to this group and shows synergistic effect with D-tagatose as shown in Examples of this invention. The compounds which do not belong to group (1) but act similarly are assumed to show synergistic effect with D-tagatose. The compounds (9-4) and (27-6) are mentioned as examples of such compounds.

Twenty five compounds belonging to group (2) and 7 compounds belonging to group (3) are a sterol biosynthesis inhibitor and they show similar synergistic effect as the representative compounds of them, simeconazole, tebuconazole and triflumizole.

Boscalid and penthiopyrad shown in Example in this invention represent a respiration inhibitor targeting on mitochondrial complex II. Metalaxyl represents a RNA synthesis inhibitor.

Benthiavalicarb-isopropyl, mandipropamid and dimethomorph represent a lipid and cell membrane synthesis inhibitor. Thiophanate-methyl is a representative compound which interacts with B-tubulin. The compound which shows synergistic effect with D-tagatose and acts similarly as those compounds mentioned above is not limited to the compounds described in Examples of this invention. The mode of action of the fungicides and moldicides which show synergistic effect with D-tagatose is wide-ranging, and the mode of action of the compounds which show synergistic effect with D-tagatose is not limited to the modes of action of the representative compounds described in Examples of this invention.

Industrially Applicability

The present invention shows that D-tagatose, belongs to monosaccharides, comprised only carbon, oxygen and hydrogen can be used as a plant disease control agent against various plant diseases and the present invention makes possible the agricultural activities with less environmental impact than conventional pesticides. And a combination of D-tagatose with other sugars and fungicidal and/or moldicidal compounds can further enhance the plant disease control efficacy. In addition, the combination with sugars and fungicidal and/or moldicidal compounds which have a different mode of action each other can contribute the plant disease control without concerning about the emergence of fungicide-resistant diseases.

The present invention can provide an excellent plant protection agent for foliar spray, soil treatment and seed treatment, and can control various plant diseases without causing phytotoxicity. The plant diseases which the present invention controls most effectively are named to be cucumber downy mildew (*Pseudoperonospora cubensis*), grape downy mildew (*Plasmopora viticola*), cucumber powdery mildew (*Sphaerotheca fliginea*), wheat fusarium blight (*Puccinia recondita*), tomato/potato phytophthora rot (Late blight of tomato and potato) (*Phytophthora infestans*), cabbage downy mildew (*Peronospora parasitica*) and rice and cucumber damping-off disease (*Pythium glaminicola, Pythium aphanidermatum*), but the plant diseases are not limited to them.

The invention claimed is:

1. A method of controlling plant disease comprising applying a plant disease controlling agent comprising D-tagatose and one or more of the members selected from the group consisting of monosaccharide, azoxystrobin, tebuconazole, triflumizole, fluopicolide, zoxamide, mandipropamid, metalaxyl, amisulbrom, propamocarb-hydrochloride, cyprodinil, dimethomorph, validamycin, kasugamycin, chlorothalonil, fthalide, fosetyl-Al, quinoxyfen, cymoxanil, tricyclazole, ferimzone, and fenamidone as an active ingredient to plants or seeds or mixing the plant disease controlling agent in soil of cultivation beds, wherein said disease is downy mildew, late blight, brown rust or rice blast.

2. The method of controlling plant diseases according to claim 1, wherein the plant disease controlling agent is applied to seeds or mixed in soil of cultivation beds.

3. The method of controlling plant diseases according to claim 1, wherein the monosaccharaide is one or more compounds selected from the group consisting of D-fructose, D-psicose, D-sorbose and D-mannose.

4. A method of controlling plant disease comprising applying a plant disease control agent comprising D-tagatose and one or more of the members selected from the group consisting of monosaccharide, fungicide, moldicide and antibiotics as an active ingredient to plants, wherein said disease is downy mildew, late blight, brown rust or rice blast.

* * * * *